United States Patent [19]

Shiokawa et al.

[11] Patent Number: 5,684,574
[45] Date of Patent: Nov. 4, 1997

[54] IN-PROCESS FILM THICKNESS MONITORING SYSTEM

[75] Inventors: Akira Shiokawa; Hideaki Yasui; Koichi Kotera; Yuuji Mukai, all of Osaka; Hiroyoshi Tanaka, Kyoto; Takashi Hirao, Osaka, all of Japan

[73] Assignee: Matsushita Electric Industrial Co., Ltd., Osaka, Japan

[21] Appl. No.: 550,853

[22] Filed: Oct. 31, 1995

[30] Foreign Application Priority Data

| Nov. 1, 1994 | [JP] | Japan | 6-268695 |
| Apr. 28, 1995 | [JP] | Japan | 7-105471 |
| Oct. 5, 1995 | [JP] | Japan | 7-259087 |

[51] Int. Cl.$^6$ ............................................. G01B 11/06
[52] U.S. Cl. .................... 356/72; 356/382; 250/559.28
[58] Field of Search ......................... 356/72, 73, 311, 356/316, 381, 382; 250/559.27, 559.28

[56] References Cited

U.S. PATENT DOCUMENTS

| 4,381,894 | 5/1983 | Gogol, Jr. et al. | 356/72 |
| 4,536,091 | 8/1985 | Allington | 356/435 |
| 4,669,873 | 6/1987 | Wirz | 356/73 |
| 4,977,330 | 12/1990 | Batchelder et al. | 250/560 |
| 4,989,970 | 2/1991 | Campbell et al. | 356/382 |
| 5,120,966 | 6/1992 | Kondo | 250/372 |
| 5,396,080 | 3/1995 | Hannotiau et al. | 250/560 |

FOREIGN PATENT DOCUMENTS

| 2 671 630 | 7/1992 | France . |
| 61-084372 | 4/1986 | Japan . |
| 02163603 | 6/1990 | Japan . |
| 03173770 | 7/1991 | Japan . |
| 05215519 | 8/1993 | Japan . |
| 07019820 | 1/1995 | Japan . |

OTHER PUBLICATIONS

Ahearn, IBM Technical Disclosure Bulletin, vol. 14, No. 1, Jun. 1971, pp. 148–149.

*Primary Examiner*—F. L. Evans
*Attorney, Agent, or Firm*—Merchant, Gould, Smith, Edell, Welter & Schmidt, P.A.

[57] ABSTRACT

A beam emitted from a light source including the characteristic wavelength of flown particles in a film forming system is interrupted by a beam chopper in a predetermined cycle, and is then divided into a probing beam and a reference beam by a beam divider. The probing beam passes through a particle flight area and is then injected into a photo detector through an optical filter, and a probing signal is outputted. A reference signal is obtained from the reference beam in the same manner. A data processor detects the phase and level of both signals, so that an absorbance, i.e., a film forming rate for the flown particles is estimated. The film forming rate is integrated with time so that a film thickness is estimated. Thus, the range of the applicable film forming rate is wide. In addition, it is possible to perform continuous monitoring with high precision also in an atmosphere where a large amount of light having the same wavelength as the characteristic wavelength of the flown particles is generated, as in sputtering systems.

18 Claims, 22 Drawing Sheets

$$\begin{pmatrix} k_{a1} & \cdots & k_{a9} \\ \vdots & \ddots & \vdots \\ k_{d1} & & k_{d9} \end{pmatrix} \begin{pmatrix} r_1 \\ \vdots \\ r_9 \end{pmatrix} = \begin{pmatrix} f\left(\dfrac{I_a}{I_{a0}}\right) & \cdots & f\left(\dfrac{I_d}{I_{d0}}\right) \end{pmatrix}$$

IN-PROCESS FILM THICKNESS MONITORING SYSTEM

FIELD OF THE INVENTION

This invention relates to an in-process film thickness monitoring system and method for online control of a film thickness in a film forming apparatus.

BACKGROUND OF THE INVENTION

In the semiconductor industry, it is essential to form a thin film by means of a film forming apparatus. Recently, it has become increasingly necessary to control a film thickness with high precision. There has mainly been used a method in which the film thickness is measured by offline instrumentation, and the time for forming a film is adjusted and managed depending on the relationship with operating parameters during film formation so as to control the film thickness in the film forming apparatus according to the prior art. As an example of an in-process film thickness monitor, a monitoring system using a quartz oscillator has been known. In a vacuum evaporation apparatus, film thickness rate control is sometimes performed by the atomic absorption method.

With reference to the drawings, there will be described a device for controlling a film forming rate by the atomic absorption method in the vacuum evaporation apparatus according to the prior art. FIG. 18 shows a schematic structure in which a light source 1 and a photo detector 3 are insulated and fixed to the outer surface of a vacuum chamber 6. The photo detector 3 has an optical filter 2 through which only characteristic wavelength light of flight particles is transmitted. The vacuum chamber 6 houses a film forming particle source 4 and a substrate 5 for forming films. There are provided a comparator 7 for comparing the output of the photo detector 3 with a preset voltage, a power supply 8 to which the result of comparison is fed back, and others.

When a predetermined amount of energy is introduced from the power supply 8 to the film forming particle source 4 in the vacuum chamber 6, the film forming material is evaporated and particles are flown. The particles thus flown are stuck to the substrate 5 to form a film. In this process, when a beam 9 including the characteristic wavelength of the evaporated material is illuminated from the light source 1 to pass through a particle flight area in the vacuum chamber 6, the intensity of the characteristic wavelength of the light is decreased depending on the number of particles (density) which exist in the beam 9. The rate of decrease, i.e., the absorbance, has a great correlation with the amount of the material evaporated from the film forming particle source 4 per unit time, i.e., a film forming rate.

The intensity of light which passed through the particle flight area in the vacuum chamber 6 and then through the optical filter 2 is detected by the photo detector 3. The absorbance is obtained from the ratio of the light intensity detected during evaporation to that detected directly before the evaporation is started. The comparator 7 compares the absorbance obtained during evaporation with a reference absorbance corresponding to the desired film forming rate obtained by an experiment in advance. If the detected absorbance is greater than the determined value, the supplied power is decreased. If the detected absorbance is smaller than the determined value, the supplied power is increased. Thus, the power supply is controlled so that the film forming rate is kept within a constant range. Consequently, it is possible to form a film having a predetermined thickness for the preset time. If outer light is mixed into the beam received by the photo detector 2, a noise is caused. The noise is cut in the following manner. More specifically, a power source 10 for driving the light source 1 generates and amplifies a rectangular wave having a TTL level at a predetermined frequency. Thus, the rectangular wave is converted into the driving current for the light source 1 and is also sent to a phase detector 11. The phase detector 11 inputs the rectangular wave as a reference signal, and detects the phase of a signal sent from the photo detector 3 to distinguish a signal detected while the light source 1 is driven from a signal detected while the light source 1 is not driven. Thus, the noise components are cut.

However, the above-mentioned apparatus according to the prior art has the following problems to be solved. More specifically, when the characteristic parameters of the film forming apparatus and the arrangement of the monitoring system are determined, the relationship between the absorbance and the film forming rate can be obtained as shown in FIG. 19. As seen from FIG. 19, the absorbance decreases greatly with the increase of the film forming rate in an area where the film forming rate is comparatively small, while the change in the absorbance is reduced when the film forming rate exceeds a certain level. Consequently, it is difficult to correspond the absorbance to the film forming rate with high accuracy.

When the system according to the prior art is applied to an apparatus in which the flight particle energy is great, such as a spattering apparatus, a large amount of excitation light having the same wavelength as the characteristic wavelength of the flown particles is generated. The excitation light thus generated is a big noise source. Consequently, even though the phase comparison is performed so as to cut noise components, the S/N ratio is considerably decreased and the dynamic range is lowered. It is difficult to fully cut the noise by the method for cutting noise components using the simple phase comparison.

In addition, the intensity of the light emitted from the light source 1 becomes unstable with time. Particles are stuck to the window of the vacuum chamber 6 through which the beam 9 is transmitted, so that the transmittance of the window is decreased. Consequently, the light intensity detected by the detector 3 becomes smaller than that to be detected. When the film forming rate control system according to the prior art is used as an in-process film thickness monitor, the above-mentioned problems are difficulties.

As described above, when the output of the power source 10 is periodically turned on and off to pulse-drive the light source 1 or sinewave-drive the same by using an alternating high voltage power source so as to cut noise components generated by outer light or the like, the light intensity of the light source easily becomes unstable with time. In addition, when a driving frequency is increased to make the measuring precision higher, the waveform of the light intensity of the light source is easily distorted.

A hollow cathode lamp utilizing the elements which make up the flight particles is not widely used for a light source. When an alloy is used for a target to form a film having plural kinds of elements, the component ratio of each element cannot be obtained. When plural sets of light sources and detectors are used, the component ratios of plural kinds of particles can be detected. However, the number of ports through which light can get access to the film forming apparatus is usually limited, In addition, the space for ports is restricted.

In the case of a monitoring system using a quartz oscillator, the flown particles cannot be specified at all.

Further, if the monitoring system is provided in a sputtering system, the life time of the quartz oscillator is short. For this reason, it is necessary to exchange the monitoring system frequently. If the monitoring system is continuously used, the temperature of the oscillator itself is increased, so that a measured value is shifted. Consequently, it is hard to continuously use the monitoring system.

SUMMARY OF THE INVENTION

It is an object of this invention to solve the above-mentioned conventional problems by providing an in-process film thickness monitoring system and method wherein the range of the film forming rate to which the system can be applied is wide, high-precision monitoring can be performed in an atmosphere, such as sputtering, where a large amount of light noise having the same wavelength as the characteristic wave length of flight particles is generated, the two-dimensional film thickness distribution for each element can be obtained, and the system can continuously be used for a long time.

In order to achieve the above-mentioned object, the in-process film thickness monitoring system of the present invention is characterized by a light source including the characteristic wavelength of flown particles in a film forming system, a beam divider for dividing a beam emitted from the light source into a probing beam which passes through the particle flight area and a reference beam which does not pass through the particle flight area, a photo detector for measuring the light intensities of the probing beam which passed through the particle scattering area and the reference beam, an optical filter for passing only the beam of the characteristic wavelength component to the photo detector, and a data processor for calculating the absorbance of the flight particles in the film forming system on the basis of a reference signal and a probing signal outputted from the photo detector and estimating a film forming rate from the absorbance.

Preferably the in-process film thickness monitoring system of the present invention further comprises a beam chopper for interrupting a beam before passing through the beam divider, and an electric filter for cutting a low-frequency component of the probing signal which is at least lower than a chopping frequency, wherein the data processor cuts the influence of noise components of the probing signal and the fluctuation in light intensity of the light source, calculates an absorbance corresponding to a film forming rate from the ratio of the intensity of the probing beam and to that of the reference beam, and estimates a film thickness by integrating the absorbance with time while film formation is performed.

A shielding plate including an aperture which has a suitable size corresponding to the film forming rate on the back of or on the same surface of a film forming substrate seen from a film forming particle source is provided in the film forming system so that the probing beam passes through the back of the aperture, or the probing beam passes through the back of the film forming substrate seen from the film forming particle source. Thus, even when a film forming rate is high, as in a sputtering process, the in-process film thickness monitoring system can be applied.

Preferably, the light source and beam divider cause a plurality of probing beams to pass through different places in the particle flight area, the photo detector measures the intensity of the probing beams which passed through the particle flight area, and the data processor estimates the two-dimensional distribution of the film forming rate or film thickness on the basis of a plurality of probing signals and reference signals outputted from the photo detector.

Preferably, there is provided a spectrometer which selects at least one of the characteristic wavelength components from the probing beam after passing through the particle flight area by means of a light source including a plurality of characteristic wavelengths when a plurality of elements are included in the flown particles in the film forming system. Probing signals are obtained for each characteristic wavelength component from the photo detector, so that the data processor estimates the film forming rate or film thickness for each element.

It is preferred that the probing beam is led to the particle flight area by means of optical fibers and the probing beam is led out of the film forming system after passing through the particle flight area by means of the optical fibers. More specifically, a frame-like head portion to which the end of an optical fiber for injection and that of an optical fiber for ejection are connected is inserted in the particle flight area in the film forming system, and the probing beam emitted from the end of the optical fiber for injection passes through the particle flight area which is restricted by the aperture of the head portion and is injected into the end of the optical fiber for ejection. Consequently, the degree of freedom is increased in case the monitoring system is attached to a vacuum chamber for forming a film.

A reflecting mirror may be provided on the head portion to increase an optical path. In addition, the optical path can be changed by the wavelength components by means of a two-way mirror or the like. Other preferred embodiments will be described below.

DETAILED DESCRIPTION OF THE INVENTION

The preferred embodiments of the present invention applied to a magnetron sputtering system will be described by referring to FIGS. 1 to 17.

Figure 1:
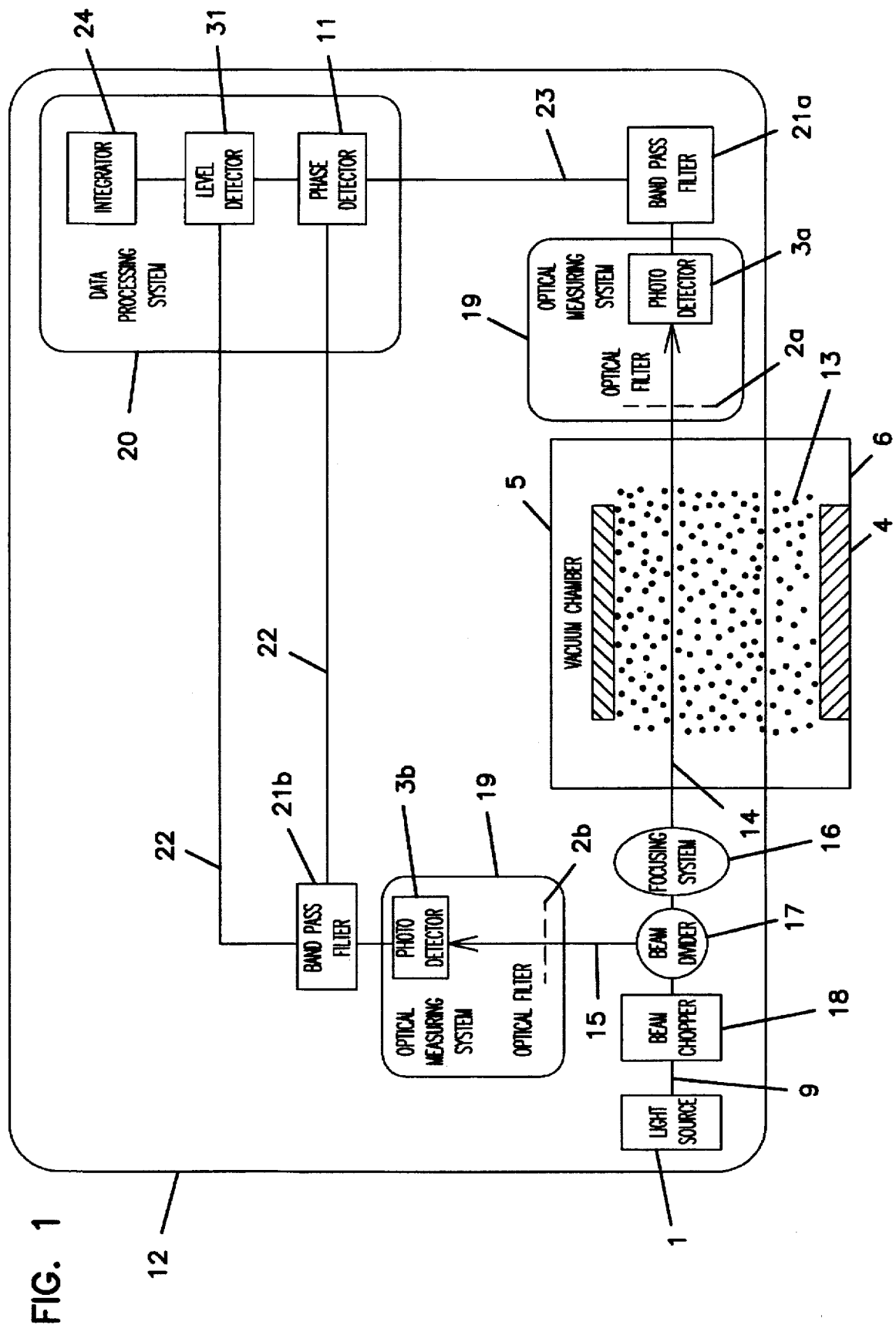
FIG. 1 is a schematic view of an in-process film thickness monitoring system according to a first embodiment of the present invention.

FIG. 1 shows the schematic structure of an in-process film thickness control system according to a first embodiment of the present invention. In FIG. 1, a beam 9 is interrupted in a predetermined cycle by beam chopper 18 and then divided into a probing beam 14 and a reference beam 15 by beam divider 17. The beam 9 is emitted from a light source 1 which generates a beam including the characteristic wavelength of scattered particles. The probing beam 14 is focused to a suitable spot size by a focusing optical system 16 and is then injected into a particle flight area 13 of a vacuum chamber 6. The spot size (beam diameter) is adjusted. Consequently, the volume of the running space of the beam 14 through the particle scattering area 13 is regulated.

The beam passes through the particle scattering area 13 and is then passed into an optical measuring system 19 which includes an optical filter 2a and a photo detector 3a.

Only a beam having a characteristic wavelength passes through the optical filter 2a. A signal corresponding to a light intensity detected by the photo detector 3a is sent to a bandpass filter 21a through which only an electric signal having a predetermined frequency band passes, and then inputted as a probing signal 23 to a data processing system 20.

The reference beam 15 is passed through an optical filter 2b which is similar to the optical filter 2a and into a photo detector 3b which is similar to the photo detector 3a. A signal corresponding to a light intensity which is detected by the photo detector 3b is inputted as a reference signal 22 to the data processing system 20 through a bandpass filter 21b which is similar to the bandpass filter 21a.

In the vacuum chamber 6, the particles which are flown from a film forming particle source 4 are stuck to a substrate 5 to form a thin film. A part of the flown particles pass through the probing beam 14 so that the light energy of the probing beam 14 is absorbed. Consequently, the light intensity detected by the photo detector 3a is decreased. The data processing system 20 estimates a film forming rate according to the decreasing ratio.

In the data processing system 20, a phase detector 11 compares the phase of a probing signal 23 and that of a reference signal 22 to cut noise components. More specifically, the probing beam and the reference beam are periodically interrupted by the beam chopper 18. It is considered that the probing signal 23 has a noise level when the reference signal 22 has a zero level. The noise level is subtracted from the level of the probing signal 23 in a period where the reference signal 22 has no zero level. As a result, the noise components are cut.

Then, the data processing system 20 computes the ratio of the level of the probing signal 23 to that of the reference signal 22 by means of a level detector 31. Consequently, an absorbance, i.e., a value corresponding to a film forming rate can be obtained at a real-time. When film formation is started, the value corresponding to the film forming rate is integrated with time. Consequently, a film thickness can be estimated. Thus, the processing for integration is carried out by an integrator 24 which is provided in the data processing system 20.

For convenience of explanation, the data processing system 20 is functionally divided into the phase detector 11, the level detector 31 and the integrator 24. Actually, a microcomputer can perform all the processing. In this case, the data processing system 20 includes an A/D converter which converts the probing signal 23 and the reference signal 22 into digital signals.

According to the system of the present embodiment, the absorbance is obtained from the ratio of the level of the probing signal 23 to that of the reference signal 22. Consequently, when the intensity of the beam 9 is varied, the intensities of the probing and reference beams are varied in the same manner. Thus, the intensity of the beam 9 is varied without influence. Accordingly, detection can be performed with high precision even though the light source varies with time.

When a large amount of excitation light having the same wavelength as the characteristic wavelength of the scattered particles is generated in a film forming atmosphere, the S/N ratio is decreased so that the dynamic range is lowered. In addition, it is hard to cut noise by phase detection. However, a bandpass filter 21b which cuts frequency components other than the frequency of the probing beam 14 is used to increase the capability of cutting noise. If the frequency is getting higher, it is hard to turn on and off the light source itself. The intensity easily becomes unstable with time. However, if the beam is interrupted by the chopper 18, the best frequency can be selected according to the condition for forming films without the above-mentioned problems.

Figure 2:
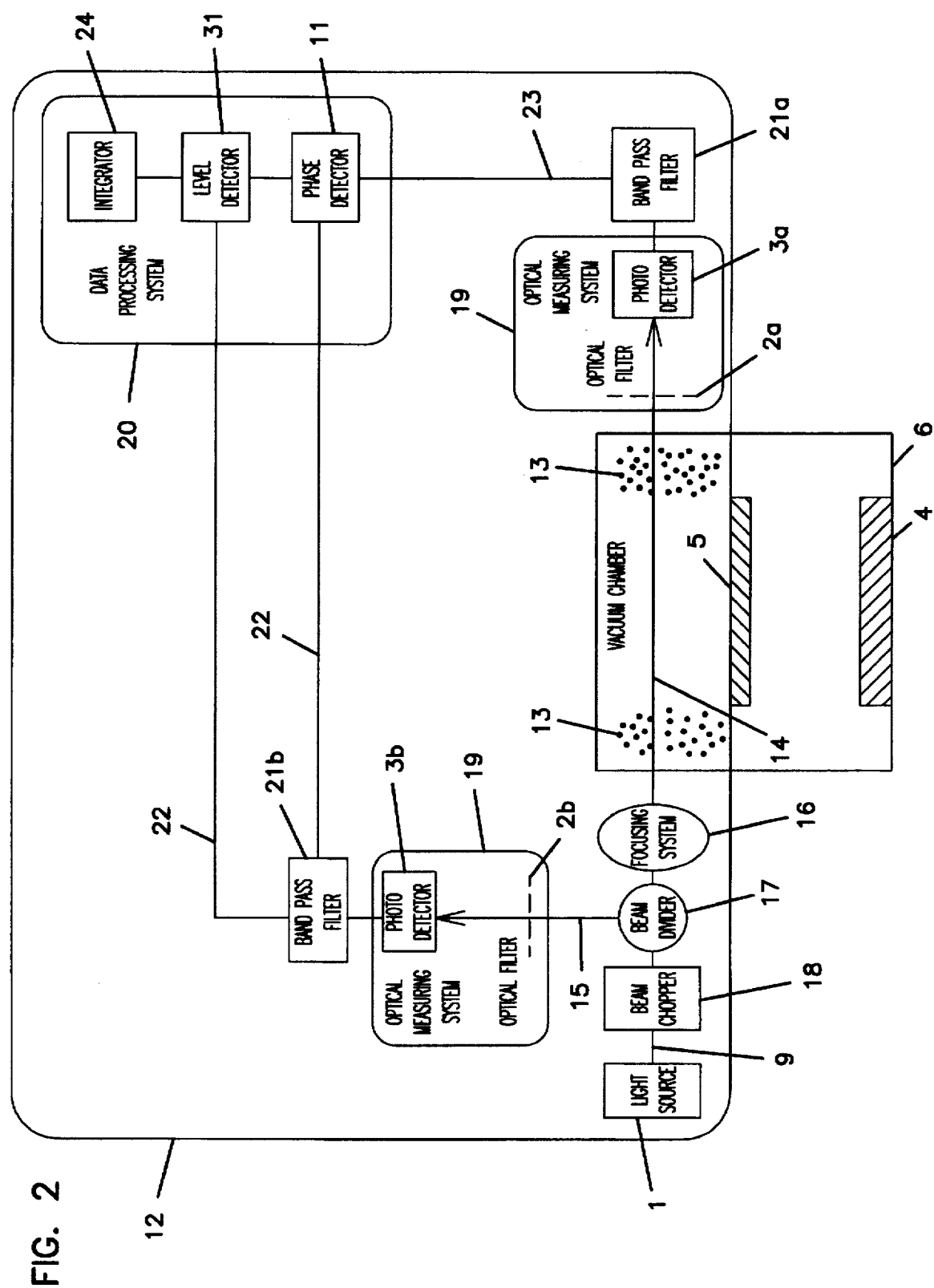
FIG. 2 is a schematic view showing a structure in which a probing beam passes through the back of a substrate so as to restrict the probing beam length through a particle flight area in the in-process film thickness monitoring system shown in FIG. 1.
Figure 3:
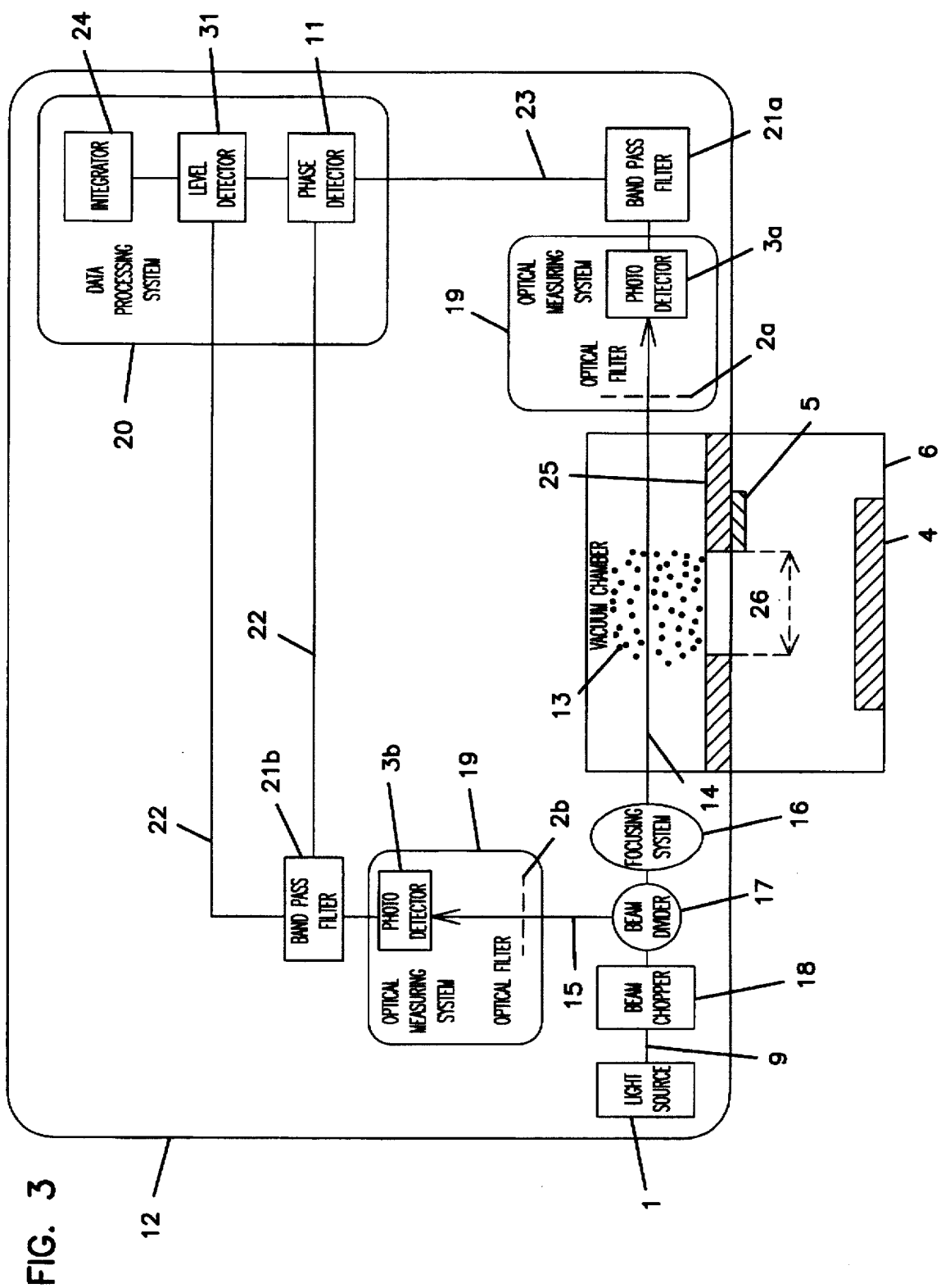
FIG. 3 is a schematic view showing a structure in which a shielding plate having an aperture is provided so as to restrict the running length of the probing beam through the particle scattering area in the in-process film thickness monitoring system shown in FIG. 1.

In FIG. 1, the probing beam 14 passes between the film forming particle source 4 and the substrate 5. As shown in FIG. 2, it is preferred that the probing beam 14 passes through the back of the substrate 5, as seen from the film forming particle source 4. Consequently, even when the film forming rate is high so that the absorbance is easily saturated, as in sputtering, a comparative small amount of particles absorb light in an area where flown particles are interrupted and restricted by the substrate 5. Consequently, the film forming rate can be estimated without the problem of absorbance saturation. As shown in FIG. 3, a shielding plate 25 having an aperture may be used to cause the probing beam 14 to pass through the back of the aperture. In this case, it is possible to vary the dimension of the aperture so that a beam length 26 of the probing beam 14 through the particle flight area 13 can be adjusted. More specifically, the beam diameter is regulated by the focusing optical system 16 and the beam length 26 is regulated, so that the volume of the space of the probing beam 14 through the particle flight area 13 can be adjusted.

The beam chopper 18 may be inserted before the beam divider 17, and the reference beam 15 may be used only for eliminating the influence of the variation in a light intensity of the light source. In this case, the reference signal for cutting the noise by phase detection can be obtained from the driving signal of the beam chopper 18.

The film thickness rate which is obtained by the in-process film thickness monitoring system of the present embodiment, and the film thickness estimation data which is obtained by the time integration of the film thickness rate, can be used as feedback data to control the supplying power for forming films as described in the prior art.

Figure 4A:
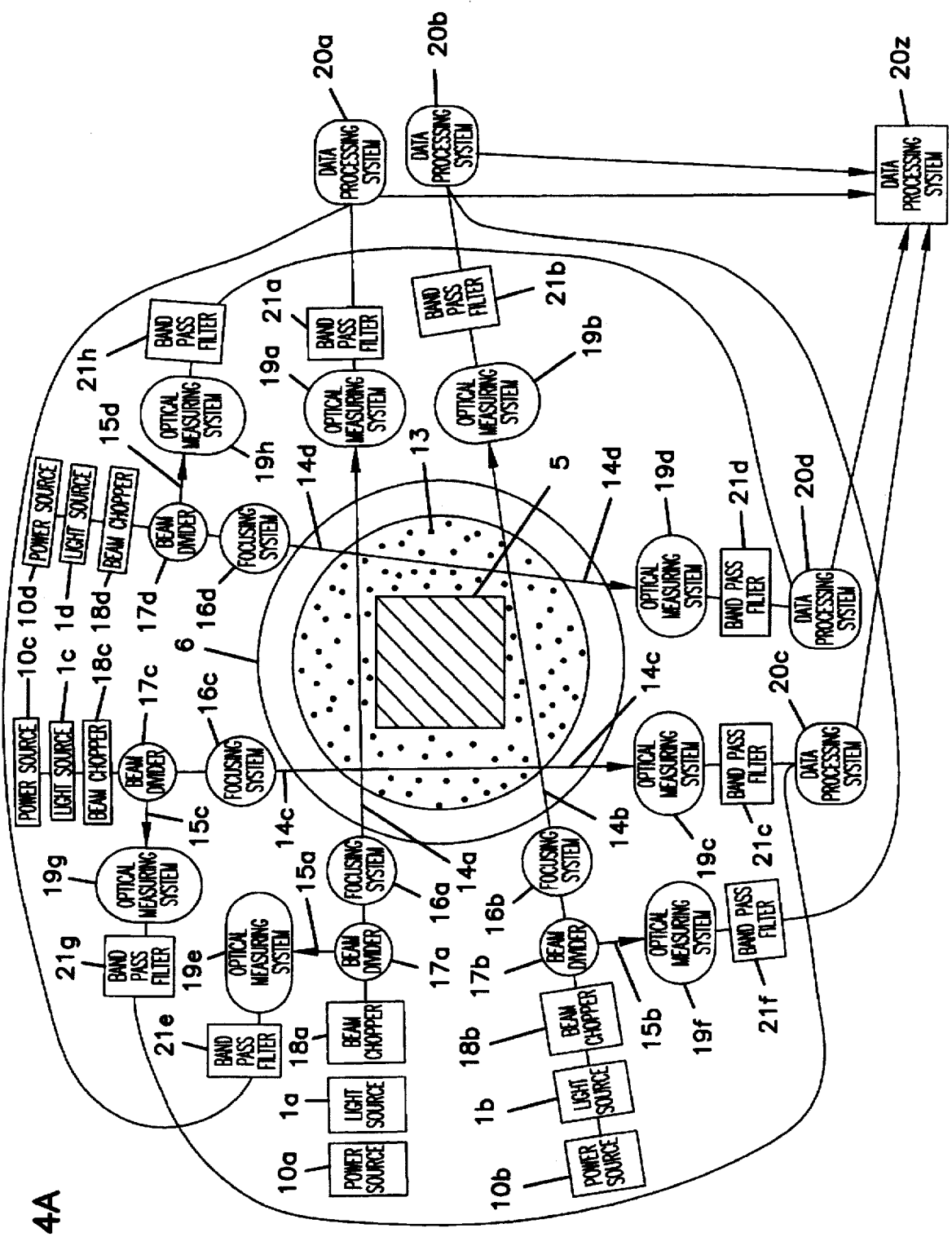
FIG. 4A is a view, seen from the particle source side, of the inside of a vacuum chamber provided in an in-process film thickness monitoring system according to a second embodiment of the present invention.

A second embodiment of the present invention will be described with reference to FIGS. 4A and B. FIG. 4A is a typical view showing the inside of a vacuum chamber seen from above. A film thickness monitoring system according to the present embodiment comprises four sets of monitoring systems shown in FIG. 1. One of the sets will be described. By way of example, a beam emitted from a light source 1a is interrupted by beam chopper 18a, and then divided into a probing beam 14a and a reference beam 15a by beam divider 17a. The probing beam 14a passes through a particle flight area 13 and then passes into an optical measuring system 19a including an optical filter and a photo detector. A signal corresponding to a light intensity detected by the photo detector is inputted to a data processing system 20a through a bandpass filter 21a. Other sets operate in the same manner. The operation has been described in detail in the first embodiment.

Data processing systems 20a to 20d get respective absorbances by means of the four sets of monitoring systems. For example, the absorbance for the data processing system 20a is the line integral value of an integral path which is the probing signal 14a in the particle flight area 13. The line integral value corresponds to the number of flown particles. The absorbances for four data processing systems are line integral values of different paths, which are normally different from one another.

Figures 4B, 4C:
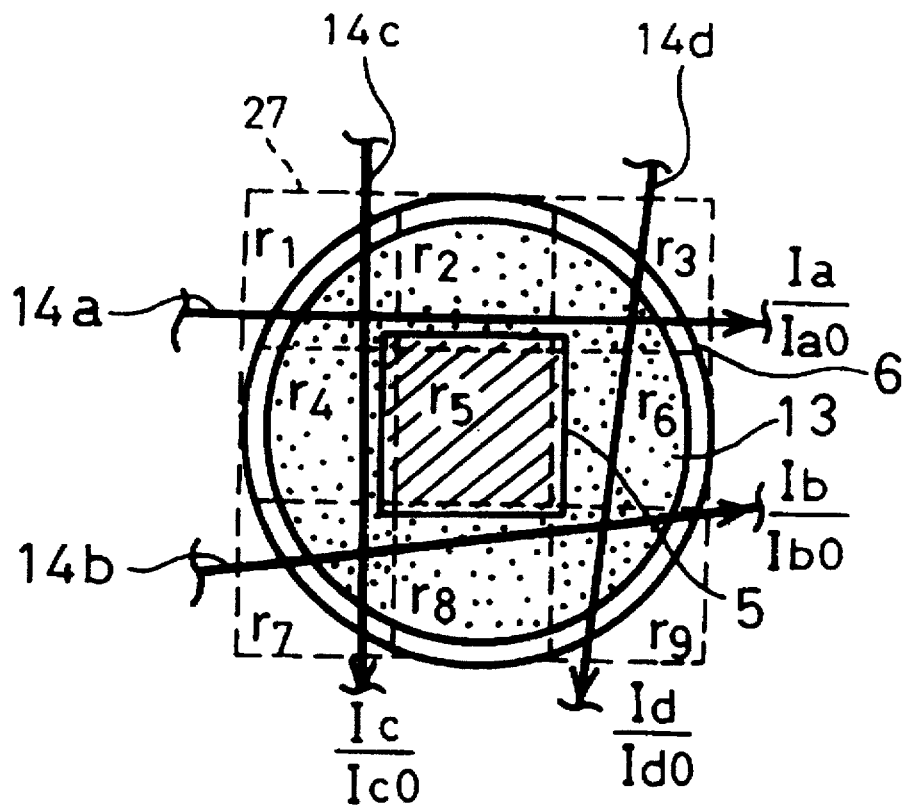
FIG. 4B is a schematic view showing how to calculate the two-dimensional distribution of the absorbance.
FIG. 4C is a matrix used in the calculation of FIG. 4B.

As shown in FIG. 4B and C, the particle flight area 13 is divided into some blocks 27 to form a matrix 28 in which the degrees of contribution of the probing beams 14a to 14d for each block 27 are numerically expressed, and then consider a column vector 29 in which the absorbance of each block, i.e., an unknown quantity, is an element. The product of the matrix 28 and the column vector 29 is a row vector of the probing beam intensities 23a to 23d which are line integral values. Accordingly, when the elements of the column vector 29, which are the unknown quantities of the determinant, are calculated, the two-dimensional distribution of an absorbance in each block 27, i.e., an absorbance (a film forming rate) in the particle flight area can be obtained. Distribution arithmetic processor 20 shown in FIG. 4A executes the processing. The film forming rate is integrated for each block 27 with time while film formation is performed, so that the two-dimensional distribution of a film thickness can be estimated.

In FIG. 4B, the particle flight area 13 is divided into nine blocks 27, and may be divided into more blocks. The number of probing beams may be more than four. According to the present embodiment, a simultaneous equation expressed by a determinant as described above is solved so that the absorbance for each block 27 can be obtained. There is a method for giving a suitable initial value to obtain an approximate value by repeat calculation. Further, the symmetric property of the two-dimensional distribution is assumed to obtain the absorbance by Abelian conversion or the like.

Figure 5A:
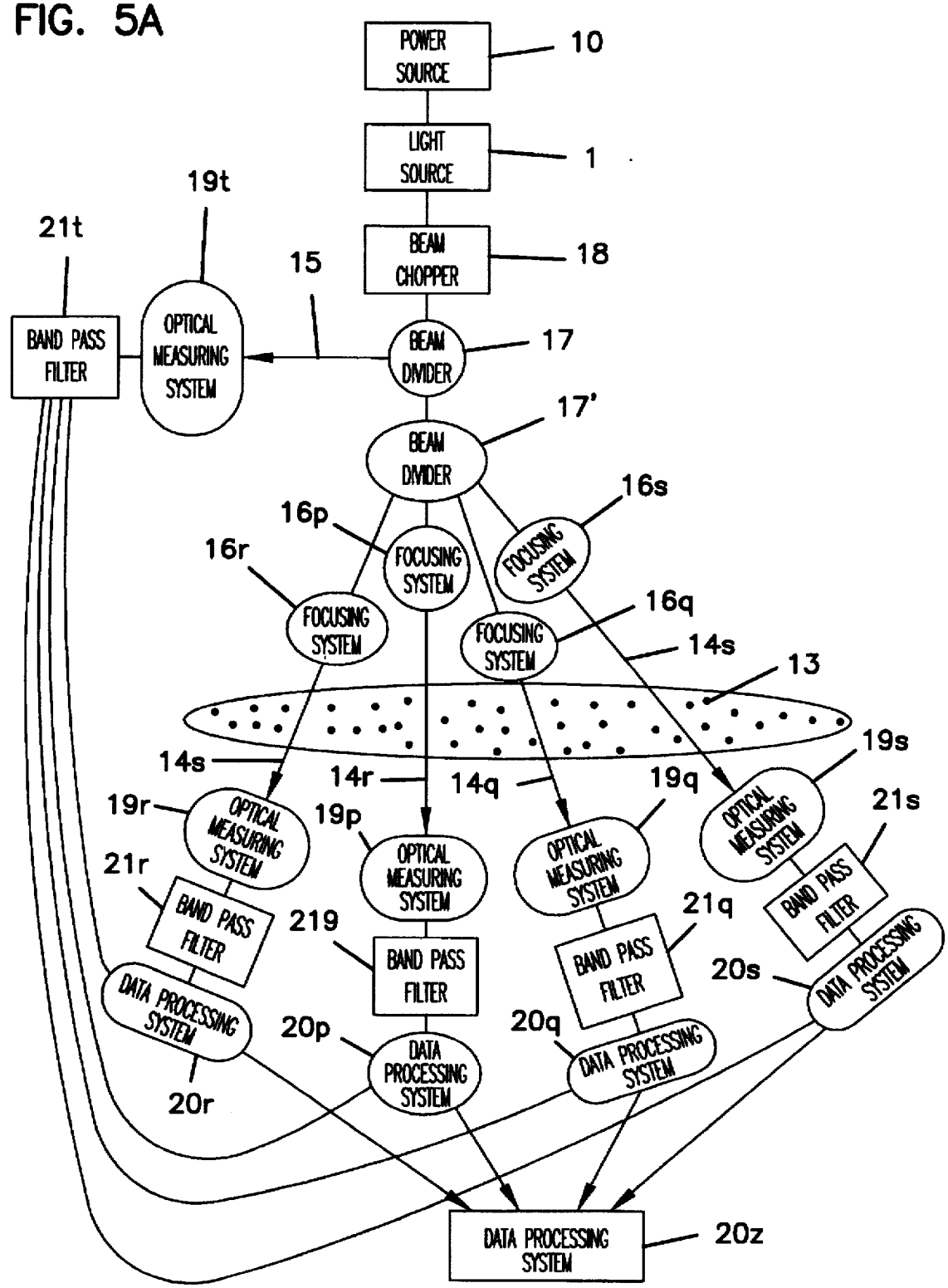
FIGS. 5A, 5B and 5C are schematic views showing examples of the method for dividing a probing beam and a reference beam in the in-process film thickness monitoring system shown in FIG. 4A.
Figure 5B:
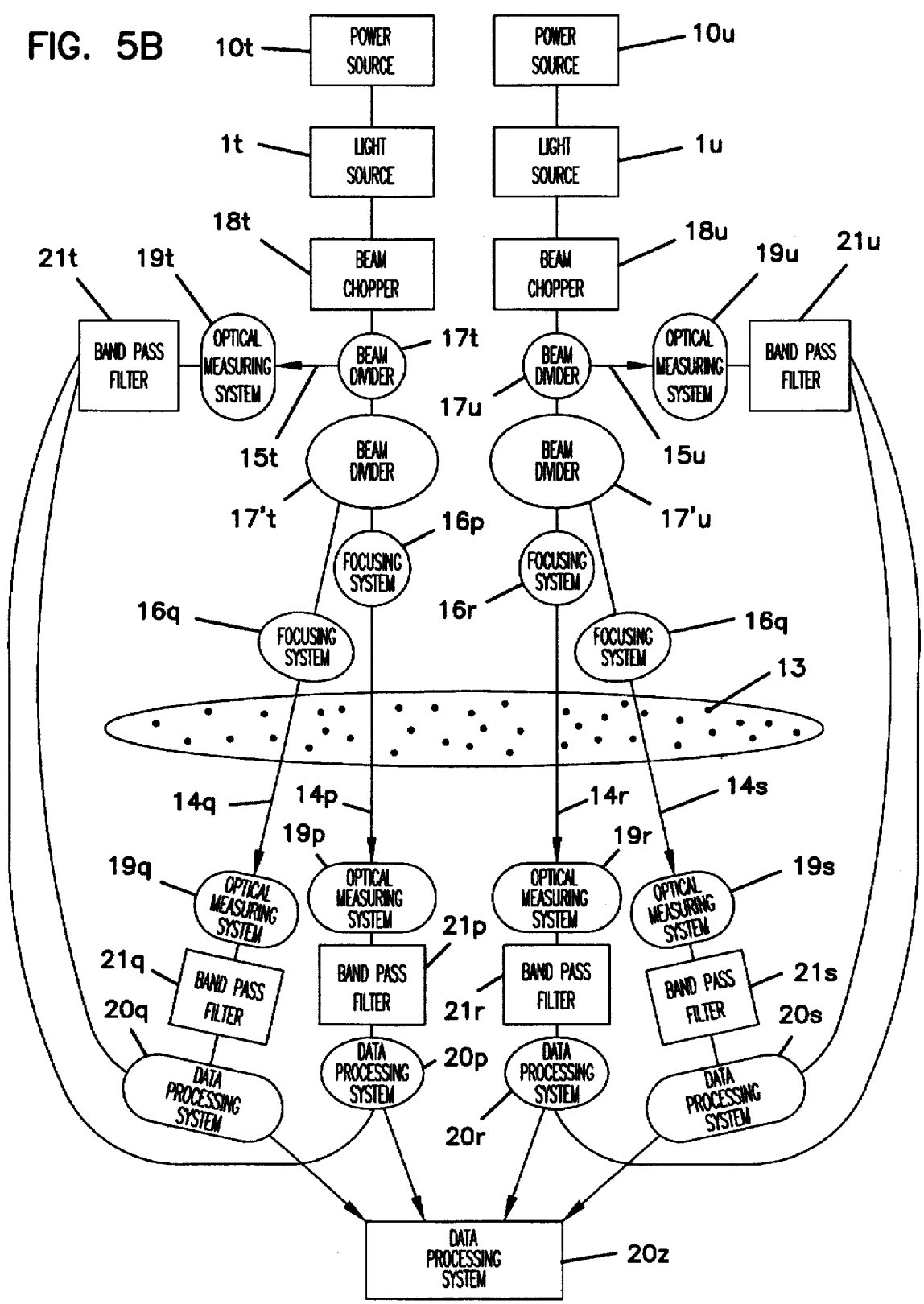
Figure 5C:
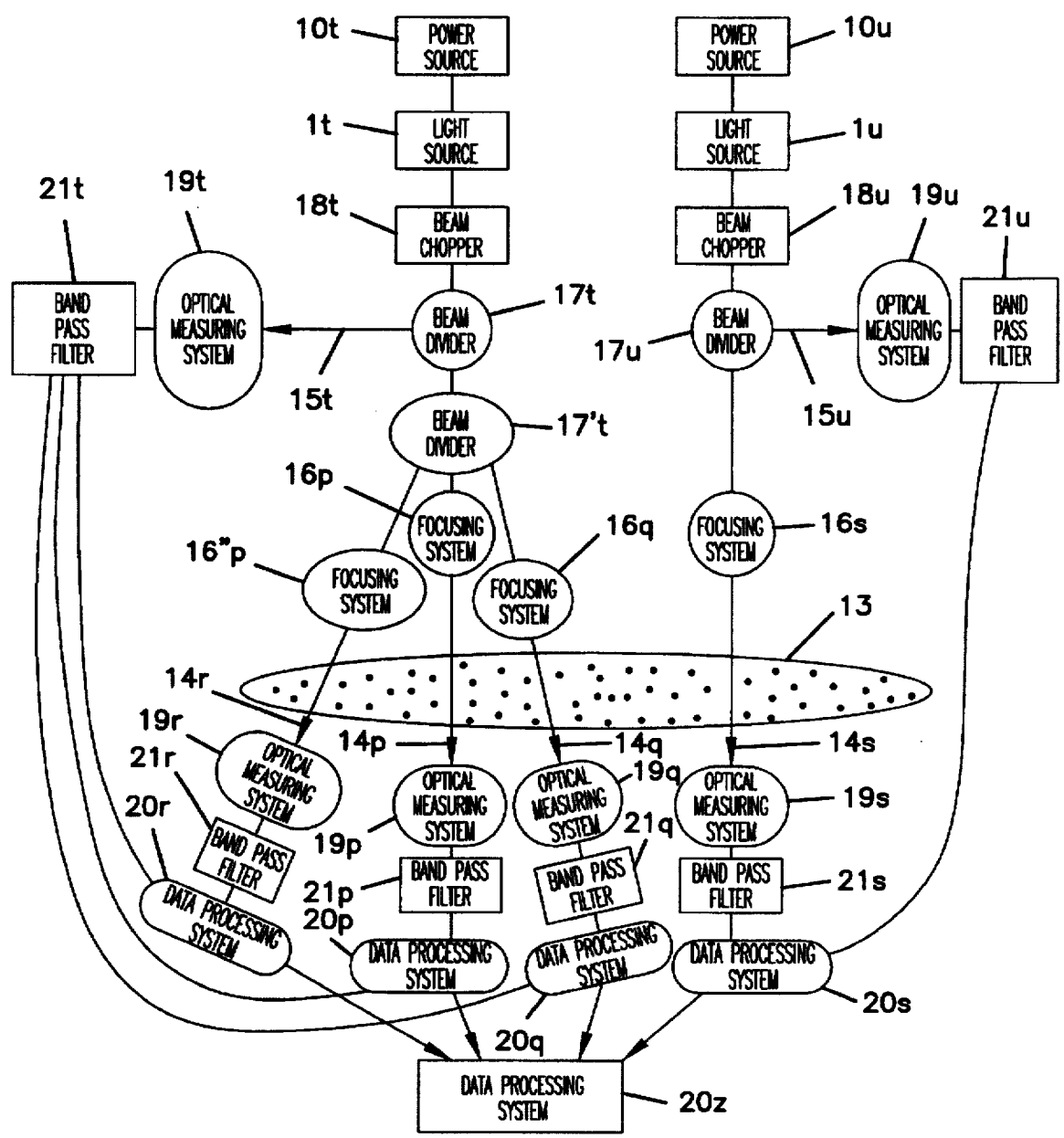

In FIG. 4A, the numbers of each of the light sources, beam choppers, beam dividers and others are the same as that of probing beams. As illustrated in FIGS. 5A to C, a beam emitted from a light source is chopped and then divided into 3 beams or more. At least one of the beams is a reference beam. Consequently, the numbers of the light sources, beam choppers, beam dividers and others can generally be decreased.

The two-dimensional distribution data for a film thickness rate and a film thickness estimated values obtained by the in-process film thickness monitoring system according to the present embodiment can be used as feedback data for controlling the power of film formation, the distance between a substrate and film forming particle sources and other parameters so as to obtain a uniform film thickness.

Figure 6:
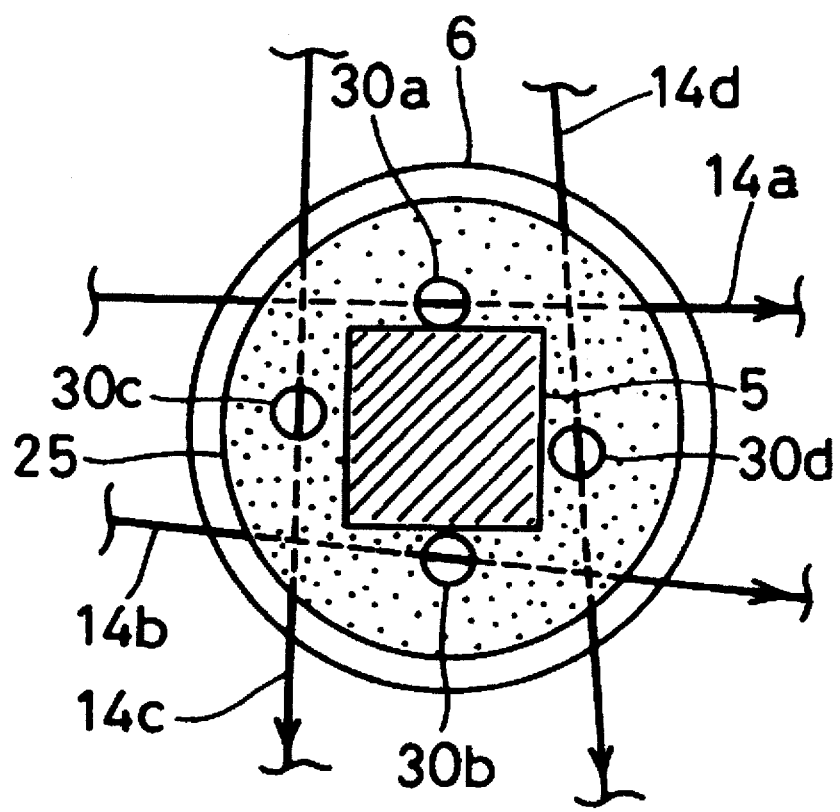
FIG. 6 is a-view, seen from the particle source side, of the inside of a vacuum chamber provided in an in-process film thickness monitoring system according to a third embodiment of the present invention.

A third embodiment of the present invention will be described with reference to FIG. 6. FIG. 6 is a typical view of the inside of a vacuum chamber seen from the film forming particle source side. A plural sets of monitoring systems are provided in the same manner as the second embodiment. However, the present embodiment is different from the second embodiment in that a shielding plate 25 having a plurality of apertures 30a to 30d is provided on the back of a substrate, as seen from the film forming particle source side, and each of probing beams 14a to 14d passes behind the shielding plate at locations corresponding to each of the apertures 30a to 30d.

By adjusting the size of each of the apertures 30a to 30d of the shielding plate 25, the beam length of each of the probing beams 14a to 14d through a particle flight area behind the shielding plate, i.e., a volume, can be regulated. The two-dimensional distribution of a film thickness rate and a film thickness can be estimated on the basis of the arrangement of the apertures 30a to 30d. If the numbers of the apertures 30a to 30d and the probing beams 14a to 14d are increased as required, the two-dimensional distribution can be estimated more finely.

Figure 7:
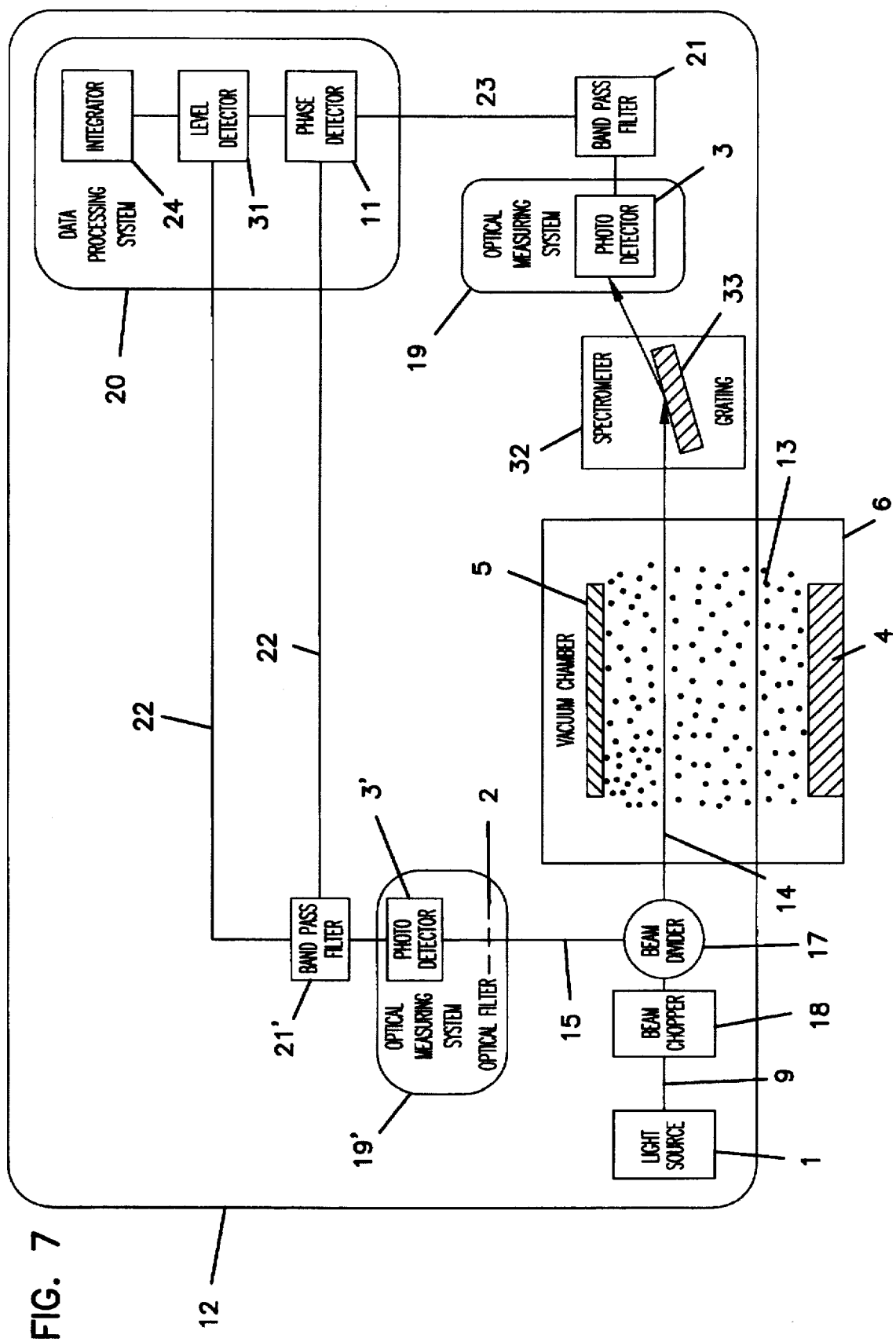
FIG. 7 is a schematic view of an in-process film thickness monitoring system according to a fourth embodiment of the present invention.

A fourth embodiment of the present invention will be described with reference to FIG. 7. The present embodiment is different from the first embodiment shown in FIG. 1 in that a monitoring system comprises a spectrometer 32 which includes a grating 33 having the function of selecting only characteristic wavelength components of a probing beam 14 and ejecting the same in the constant direction. In this case, an optical filter through which only the characteristic wavelength beam is transmitted to an optical measuring system 19 can be omitted.

The operation of a film thickness monitoring system according to the present embodiment is basically the same as the operation described in the first embodiment. There will be mainly described the difference between the present embodiment and the first embodiment, and complements.

Beam chopper 18 interrupts a light source beam 9 in a predetermined cycle. Accordingly, a reference beam 15 obtained by beam divider 17 is injected into an optical measuring system 19, so that a reference signal 22 is obtained. The reference signal 22 is a signal having the form of a rectangular wave. The reference signal 22 is inputted to a phase detector 11 and a level detector of a data processing system 20. The level detector includes a sample hold circuit, and can properly get the time variation of the light intensity of a light source for a sampling frequency which is lower than a chopping frequency. Thus, the information about a phase and a light intensity is obtained from the reference signal 22 so as to correct a probing signal 23. Consequently, the influence of the light intensity variation of the light source beam 9 and noise components are cut so that measuring precision can be enhanced.

The phase detector 11 of the data processing system 20 regards, as a noise level, the level of the probing signal 23 obtained when the level of the reference signal 22 is zero, and subtracts the noise level from the level of the probing signal 23 obtained when the level of the reference signal 22 is not zero. The following operation is carried out to correspond to the case in which the phase difference between the reference signal and the probing signal is varied with time. First, multiplication is carried out by a PSD circuit (a phase detection circuit having semi-heterodyne form) provided in the phase detector 11. Then, a sine wave having a suitable frequency is generated. Multiplication is carried out again by using the sine wave. Thus, phase correction is performed in case there is the phase difference between the probing and reference signals. The phase difference between the probing and reference signals may be generated by small signal delay caused by the difference in impedance or the lengths of signal cables. Instead of second multiplication, one of the signals is delayed to match their phases. Then, multiplication is carried out by the PSD circuit. Consequently, it is possible to omit a second multiplication circuit which greatly influences the measuring precision. It is desired that the reference signal is delayed. Further, a circuit for controlling the delay time so as to automatically match the phases can be used.

When a large amount of the same wavelength as the characteristic wavelength of flown particles is generated as excitation light or the like in the film forming atmosphere, the S/N ratio is considerably decreased and the dynamic range is lowered. Further, noise components cannot fully be cut by phase comparison. For this reason, the frequency components other than the driving frequencies of the probing beam 14 and the reference beam 15 are cut from the output of a photo detector 3 in advance and are inputted to a phase detector 11. It is necessary to consider the variation in noise beam, as a noise source, caused by the ripple of components used for a power supply for a film forming system.

For example, if a film is formed by means of a DC sputtering power source and a single-phase, 200V input DC sputtering power source, 60 Hz, three-phase, 200V input is converted into a DC current, so that a 360 Hz ripple component is generated, and 60 Hz, single-phase 200V input is converted into a DC current, so that a 120 Hz ripple component is generated. The 60 Hz noise component also exists due to a main power. Therefore, the frequency components of 60 Hz, 120 Hz and 360 Hz, and a DC are removed by using a bandpass filter. Consequently, the time response of signals can be enhanced and the distortion of rectangular signals is reduced compared with a method using a conventional filter which removes all the frequency components but components in the proximity of a signal frequency.

When a rectangular wave passes through the bandpass filter to cut low-frequency noise components, signals in portions other than the leading edge and trailing edge of the rectangular wave are regarded as DC components. Consequently, the distortion of the output waveform of the bandpass filter is increased. An integrator which can vary an integral time constant is inserted to perform waveform shaping. Then, the wave thus shaped is inputted to a lock-in amplifier. Thus, the operation of the lock-in amplifier is stabilized.

The light source is not turned on and off, but beams are interrupted by the beam chopper 18. Consequently, a light intensity is stabilized so that a beam having a stable intensity can be obtained. It is also possible to modulate the driving frequency of the beam chopper 18 with time so as to select the best frequency corresponding to film forming conditions. In case of on and off driving, the light source itself is first turned on by a DC or a low frequency of several Hz and the frequency is gradually increased. Consequently, the light source can be turned on comparatively stably.

Figure 8:
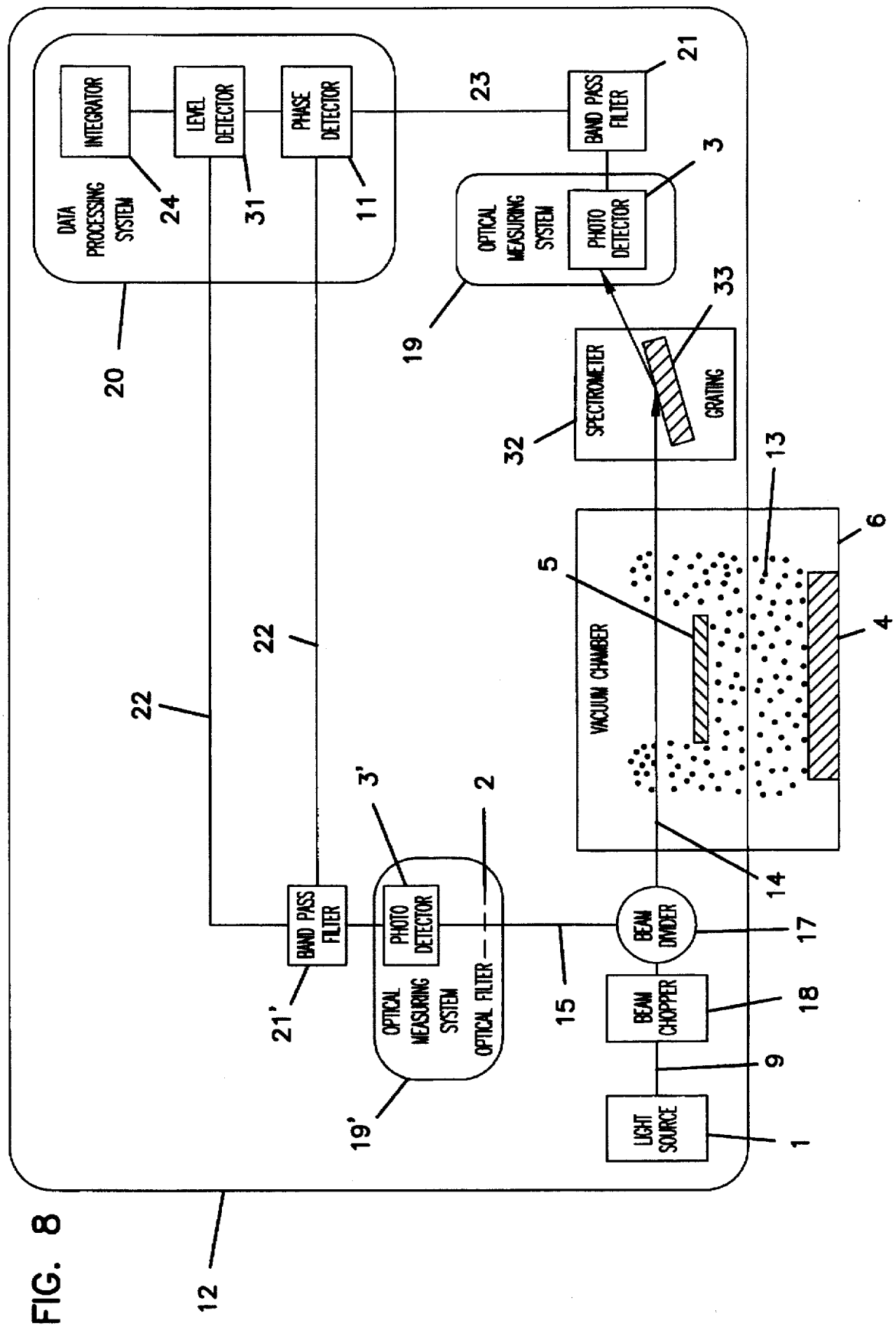
FIG. 8 is a schematic view showing a structure in which a probing beam passes through the back of a substrate so as to restrict the beam length of the probing beam through a particle scattering area in the in-process film thickness monitoring system shown in FIG. 7.
Figure 9:
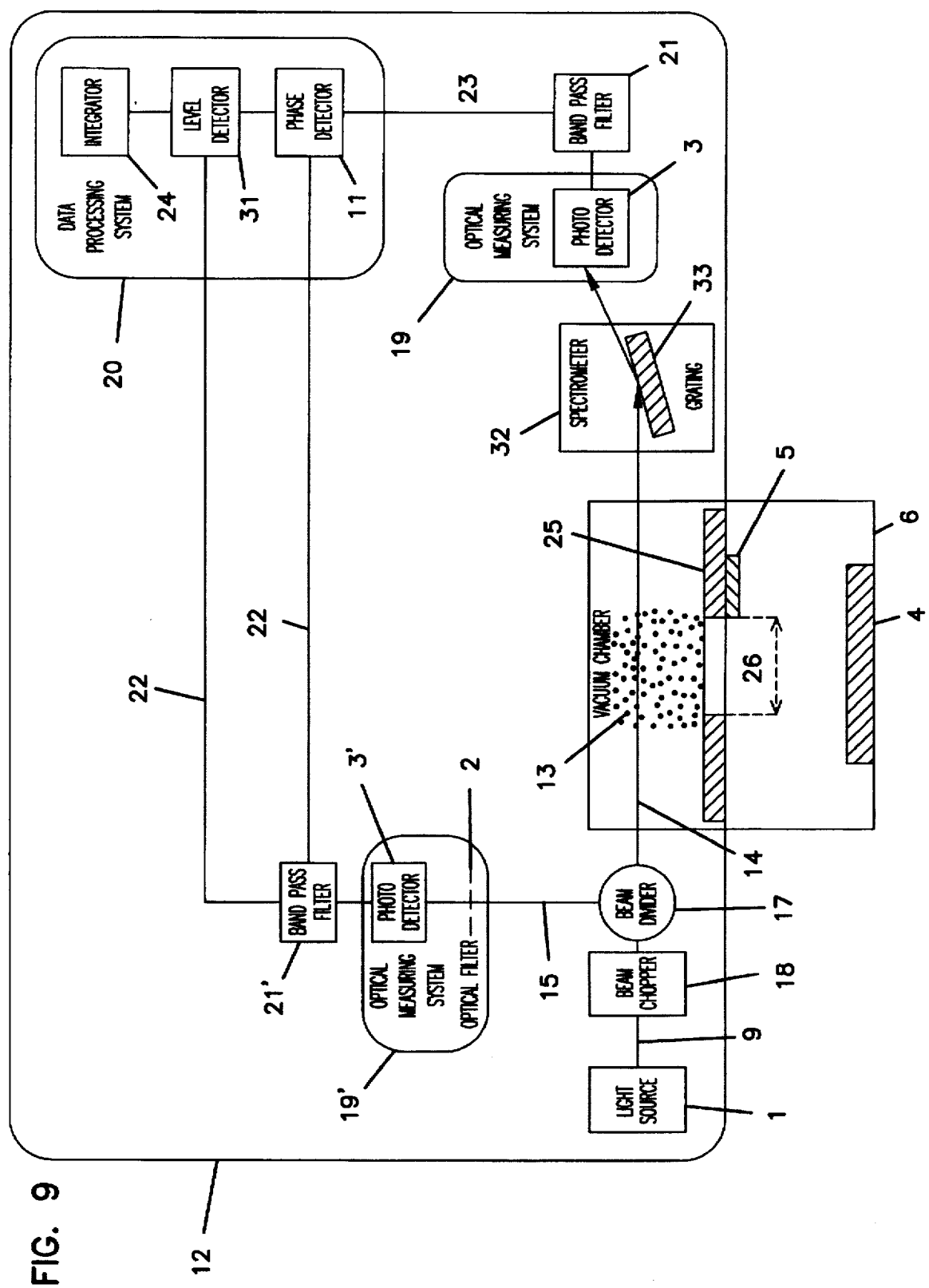
FIG. 9 is a schematic view showing a structure in which a shielding plate having an aperture is provided so as to restrict the length of the probing beam through the particle scattering area in the in-process film thickness monitoring system shown in FIG. 7.

In the same manner as the first embodiment, when a film forming rate is high so that an absorbance is easily saturated, the probing beam 14 is caused to pass through an area behind the substrate 5, again as seen from a film forming particle source 4, as shown in a variant of FIG. 8, so that the film forming rate can be estimated without saturation. As shown in FIG. 9, a shielding plate 25 having an aperture may be provided, with the probing beam 14 passing behind the plate. In this case, the dimension of an aperture is varied so that a beam length 26 of the probing beam 14 through the particle flight area 13 can be regulated.

While a focusing optical system provided next to a beam divider 17 is omitted in the present embodiment, it is preferably provided in the same manner as the first embodiment. The embodiment of FIG. 9 also includes peak hold circuit 34, which accepts the rectangular reference signal from the bandpass filter 21' and outputs a DC reference level 35 to level detector 31.

Figure 10:
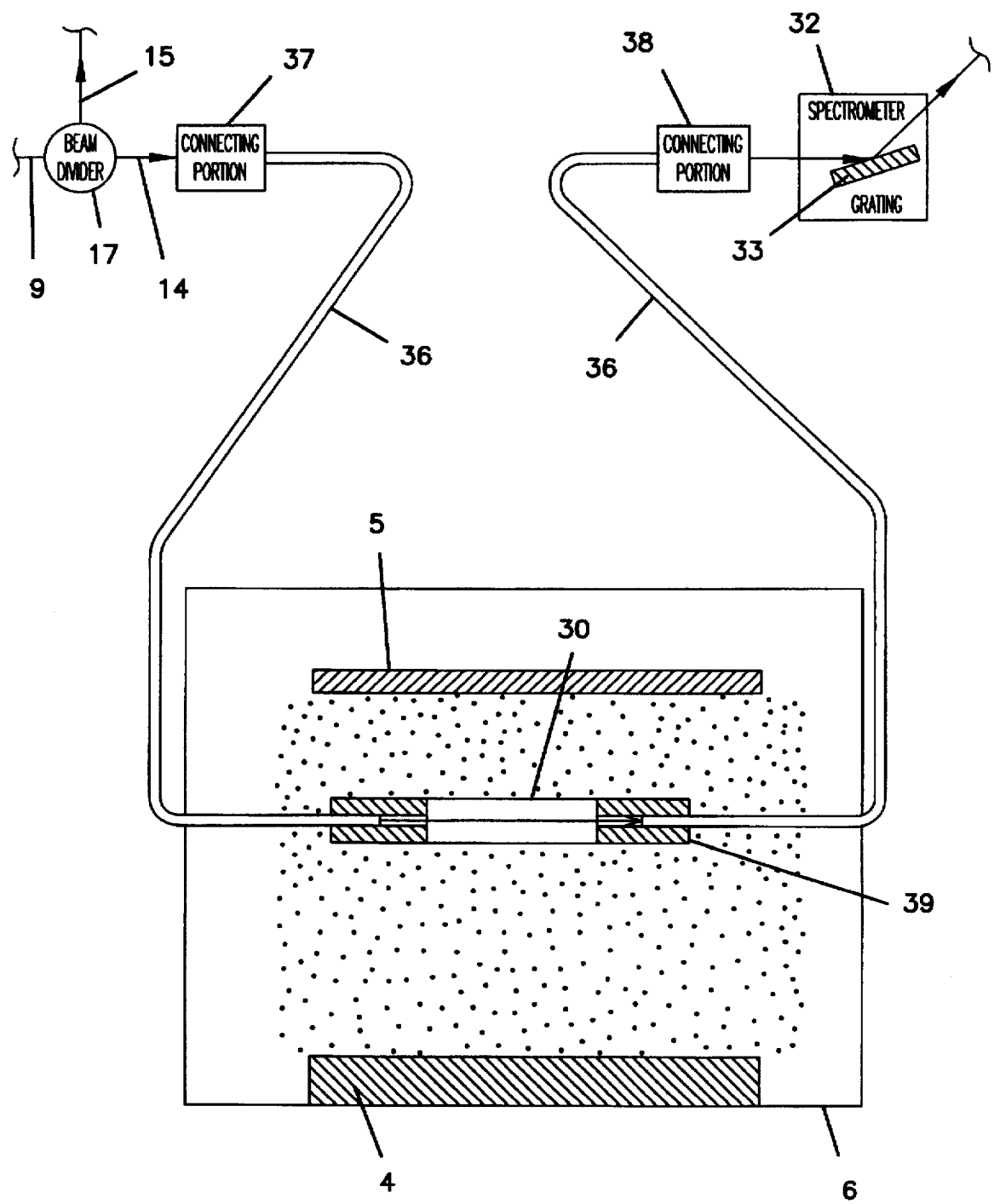
FIG. 10 is a schematic view showing a structure in which the probing beam is led into a vacuum chamber by an optical fiber and the probing beam is led out of the vacuum chamber by the optical fiber after passing through the particle flight area in the in-process film thickness monitoring system shown in FIG. 7.

According to the present embodiment, a window is provided on the wall opposite to a vacuum chamber so as to transmit the probing beam. If it is hard to form the window, optical fibers 36 for injection and ejection connected to a frame-like head portion 39 having an aperture 30 may be inserted into the vacuum chamber as shown in FIG. 10. The probing beam is injected into the optical fiber 36 for injection through a connecting portion 37, and then propagated in the optical fiber 36 and led to the head portion 39. The probing beam ejected from the optical fiber 36 on the head portion 39 passes through the particle flight area which is restricted by the aperture 30 of the head portion 39. Then, the probing beam is injected into the optical fiber 36 for ejection, propagated in the optical fiber 36 and led to a spectrometer 32 through a connecting portion 38. In this case, the size of the aperture 30 of a beam injection and ejection member 39 is adjusted to correspond to a wide film forming rate range. By way of example, in case the film forming rate is high so that it is necessary to reduce the beam length of the probing beam through the particle flight area, the size of the aperture 30 can be reduced. It is possible to put optical systems in one place by using optical fibers and keep them away from a film forming system.

A fifth embodiment of the present invention will be described with reference to FIG. 11. The present embodiment is different from the fourth embodiment shown in FIG. 7 in the following respects. More specifically, a probing beam which passed through a particle flight area 13 is divided into a plurality of wavelength components corresponding to the characteristic wavelengths of a plurality of atoms by a spectrometer 32 including a grating 33. A plurality of optical measuring systems 19 to which the divided beams are injected are provided so that the intensity of the probing beam can be measured for each kind of atoms.

According to a film thickness monitoring system having the above-mentioned structure, if a flown particle has a plurality of elements, as in sputtering in which an alloy is used as a target, an absorbance for each element, i.e., a film forming rate, can be detected.

Figure 11:
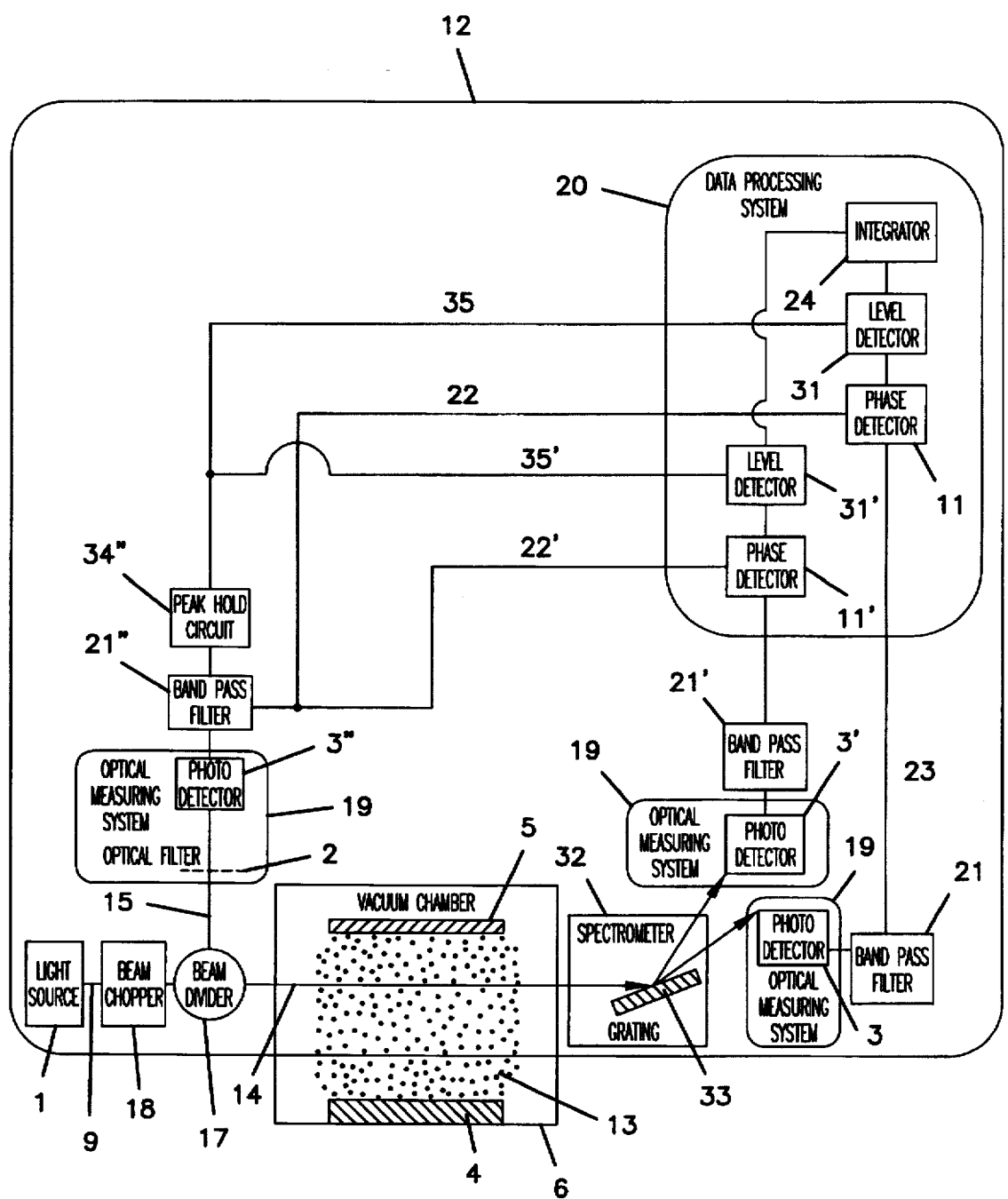
FIG. 11 is a schematic view showing a structure in which the film thickness of each element particle is monitored in an in-process film thickness monitoring system according to a fifth embodiment of the present invention.

As shown in FIG. 11, optical measuring systems 19 and 19' are provided. A probing signal 23 can be obtained for two kinds of wavelength components. A data processing system 20 comprises phase detectors 11 and 11' and level detectors 31 and 31', and obtains the absorbance by cutting noise components for each wavelength component and correcting the variation in light source. Also, when the numbers of each of the spectral channels and optical measuring systems are three or more, the same operation is carried out.

If the film thickness monitoring system of the present embodiment is used for forming a film having a single element, a plurality of different characteristic wavelengths for the same element are selected and a plurality of data thus obtained are processed so that the measuring precision can be enhanced. In a spectrometer using a grating, the change of a film forming rate is repeated in a shorter cycle than the expected cycle and the angle of the grating is varied within the range in which the light intensity of a necessary wavelength can be detected. Thus, a plurality of wavelengths may be monitored by a single optical measuring system.

Figure 12:
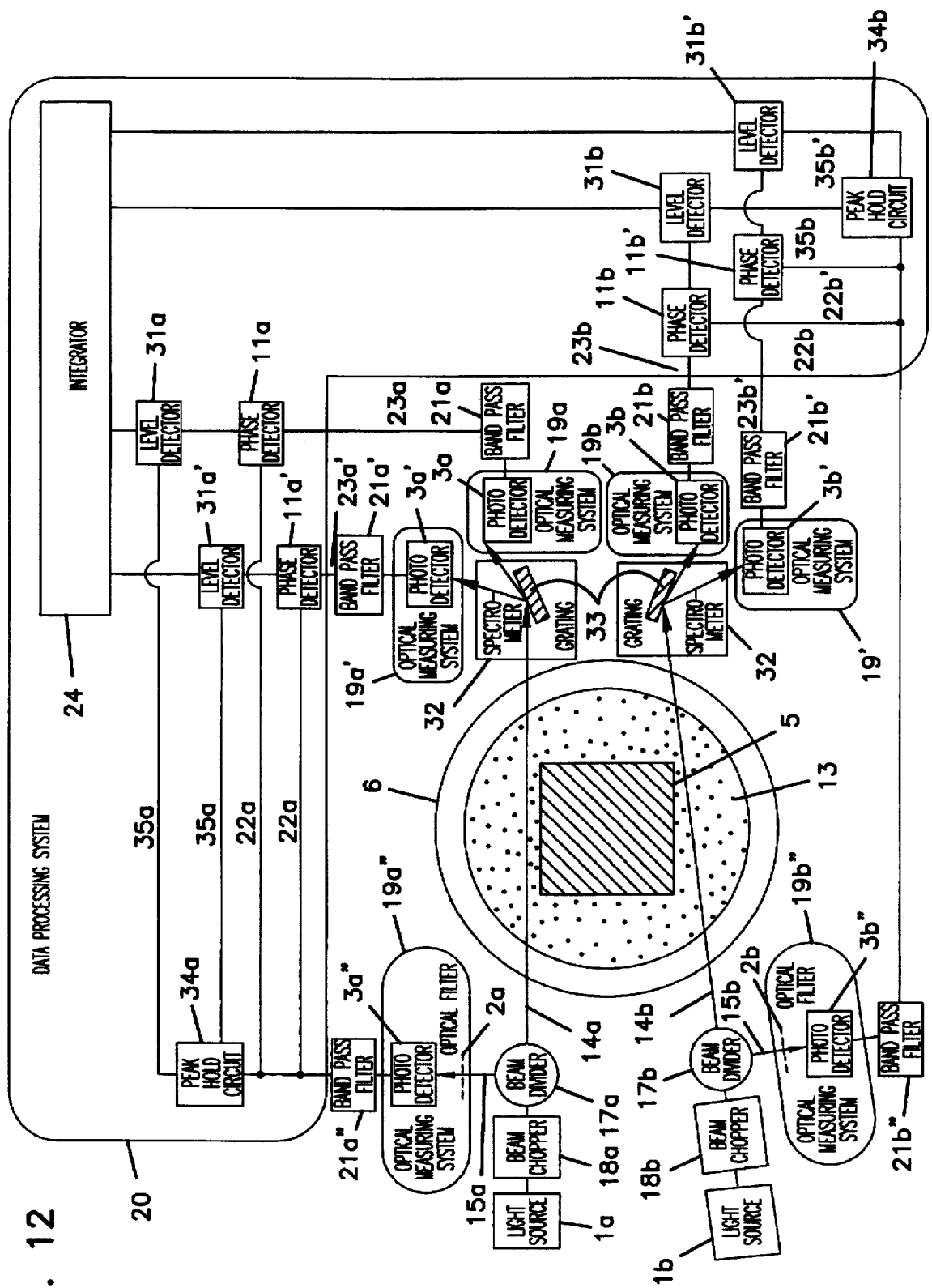
FIG. 12 is a schematic view of an in-process film thickness monitoring system according to a sixth embodiment of the present invention.

FIG. 12 shows a sixth embodiment of the present invention. FIG. 12 is a typical view showing the inside of a vacuum chamber seen from above. A film thickness monitoring system according to the present embodiment is formed by the combination of the second embodiment shown in FIG. 4 and the fifth embodiment described above. More specifically, the two-dimensional distribution of absorbances can be measured by means of plural sets of monitoring systems. A spectrometer 32, a plurality of optical measuring systems and others are provided for each set. Consequently, the two-dimensional distribution of an absorbance, i.e., a film forming rate can be obtained for each wavelength component corresponding to a plurality of elements.

Figure 13:
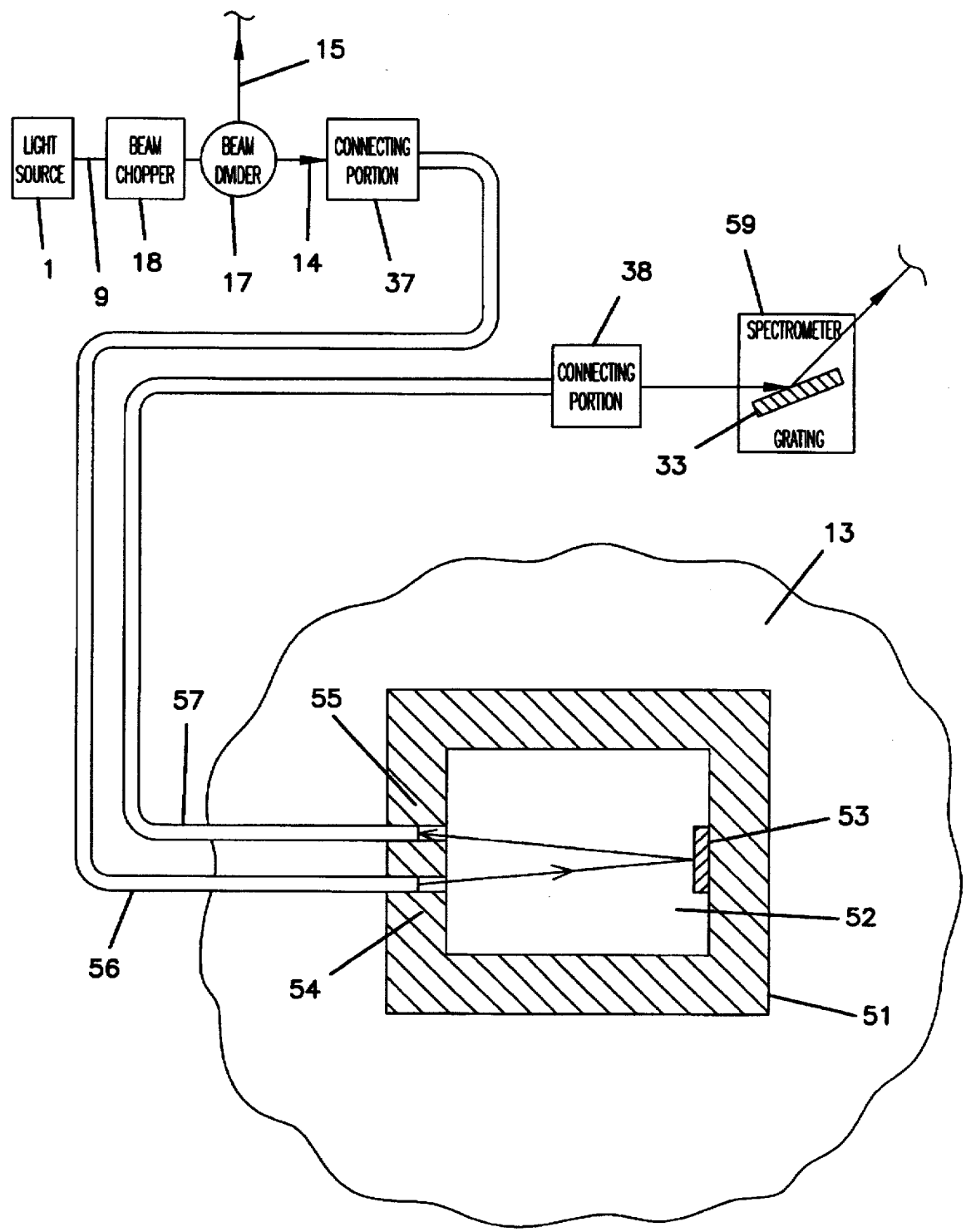
FIG. 13 is a schematic view mainly showing the head portion of an in-process film thickness monitoring system according to a seventh embodiment of the present invention.

A seventh embodiment of the present invention will be described with reference to FIG. 13. FIG. 13 shows a head portion 51 which is inserted into a particle flight area 13 in a vacuum chamber. The head portion 51 includes a frame which surrounds an aperture 52, a reflecting mirror 53 fixed onto the inner wall thereof, and optical fiber connecting portions 54 and 55 for injection and ejection which are provided on the inner wall opposite to the reflecting mirror 53. In the same manner as each embodiment described above, a beam 9 having the characteristic wavelength of flown particles is emitted from a light source and interrupted in a predetermined cycle by a beam chopper, and then divided into a probing beam 14 and a reference beam 15 by a beam divider 17. The probing beam 1 is injected into an optical fiber 56 for injection which is connected through an injection connecting member 37, and propagated in an optical fiber 56 and then led to the head portion 51. In the head portion 51, the probing beam 14 ejected to the aperture 52 through the optical fiber connecting portion 54 is reflected by the reflecting mirror 53 fixed onto the inner wall of the frame which surrounds the aperture 52, and then injected into an optical fiber 57 for ejection through the optical fiber connecting portion 55. The beam which is propagated in the optical fiber 57 is led into the same optical system as in each embodiment described above through a connecting member 38 for ejection and a spectrometer 59 (grating 33). Thus, processing is carried out.

The probing beam 14 goes to and comes back from the aperture 52 of the head portion 51 inserted into the particle flight area 13 in the vacuum chamber. The light energy of the probing beam 14 is absorbed by flown particles which exist in an optical path. When the absorbance is detected, a film forming rate can be measured in the same manner as the embodiments described above.

The flown particles in the particle flight area 13 are separated, at a constant rate, into respective ones which pass or do not pass in the probing beam 14 by means of the aperture 52. Consequently, even though the film forming rate is high, the film thickness monitoring system of the present embodiment can be applied within the range in which the absorbance is not saturated. In the case of a film thickness monitoring system according to the present embodiment, a single place through which optical fibers for injection and ejection pass may be provided on the wall of the vacuum chamber. The position of the place has a relative degree of freedom. Consequently, if it is structurally hard to cause the probing beam to pass through a window provided on the wall opposite to the vacuum chamber as described above, the film thickness monitoring system of the present embodiment is effective.

By adjusting the size of the aperture 52 of the head portion 51, the film thickness monitoring system of the present embodiment can correspond to film forming rates within a wide range. A plurality of mirrors are sequentially shifted and placed on the inner wall opposite to the head portion 51 so that the number of reflections of the probing beam 14 in the aperture 52 can be increased. By adjusting the number of reflections, the film thickness monitoring system of the present embodiment can correspond to a film forming rate within a wide range. The outer shape of the head portion 51 and the form of the aperture are not limited to a rectangle but can be varied.

It is possible to provide means for moving the head portion 51 in the particle flight area 13 and controlling the position thereof so as to measure the two-dimensional distribution of the film forming rate.

The variants described in the above embodiments can be applied to the present embodiment. More specifically, a beam passes through a spectrometer and the light intensities of a plurality of wavelength components are detected by a plurality of photo detectors so as to measure film forming rates for a plurality of elements.

Figure 14:
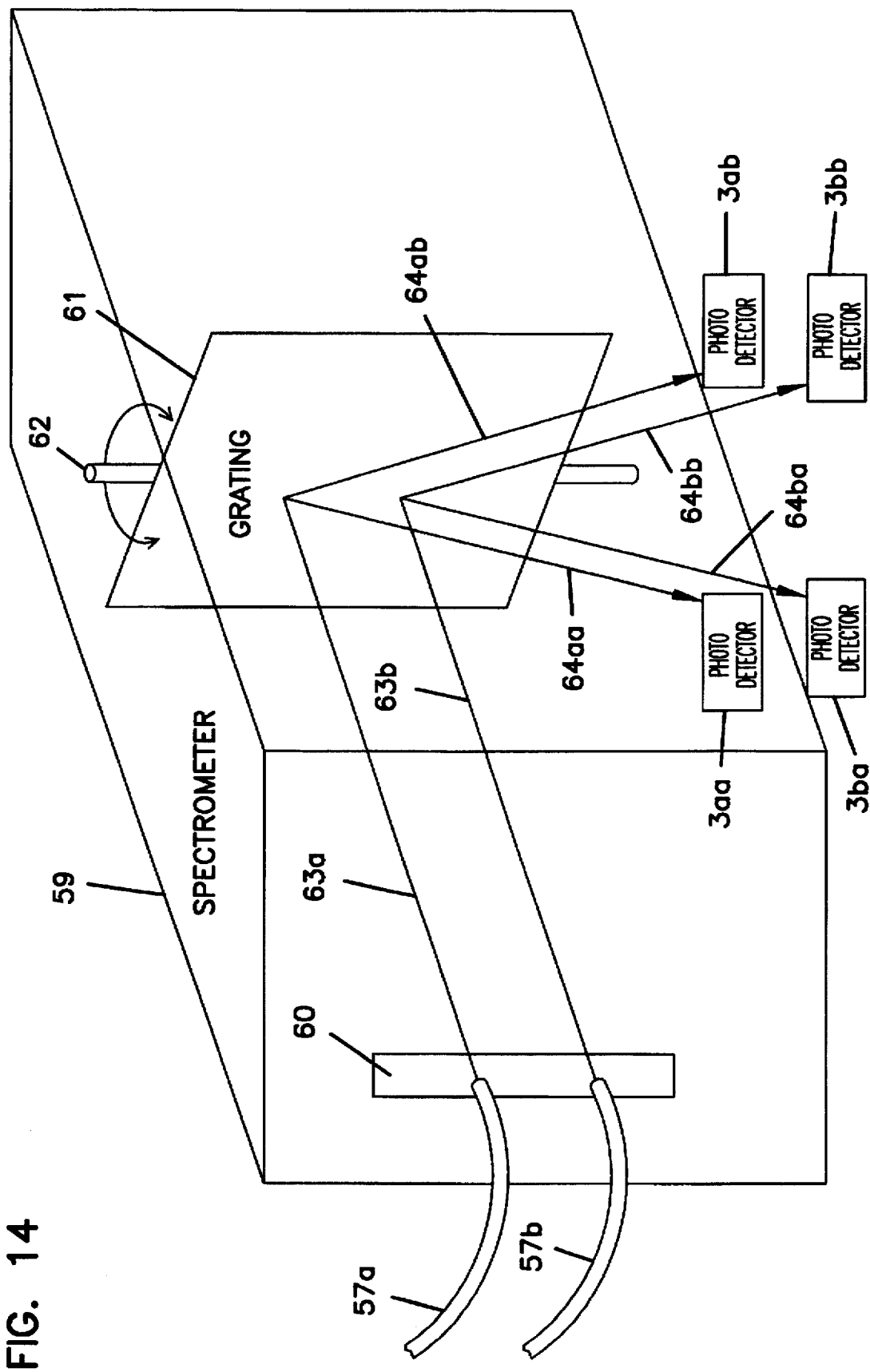
FIG. 14 is a schematic view showing a structure in which signals sent from a plurality of optical fibers are divided by a spectrometer in the in-process film thickness monitoring system shown in FIG. 13.

As a variant of the present embodiment, a plurality of optical fibers 57a and 57b which come out of one or more head portion(s) inserted into the particle flight area 13 may be provided along an inlet slit portion 60 of a spectrometer 59 with a predetermined space kept therebetween as shown in FIG. 14. The inlet slit portion 60 is provided almost in parallel with a rotary shaft 62 of a grating 61 in the spectrometer 59. Beams 63a and 63b ejected from the optical fibers 57a and 57b are directed perpendicularly to the rotary shaft 62 and parallel to and spaced from each other so that they do not interfere with each other. The beams 63a and 63b are reflected and divided into beams 64aa to 64bb by the grating 61. Photo detectors 3aa to 3bb for individually detecting light intensities are provided in positions corresponding to the beams 64aa to 64bb. FIG. 14 shows a case in which two beams ejected from two head portions are processed. Three beams or more can be processed in the same manner.

Figure 15:
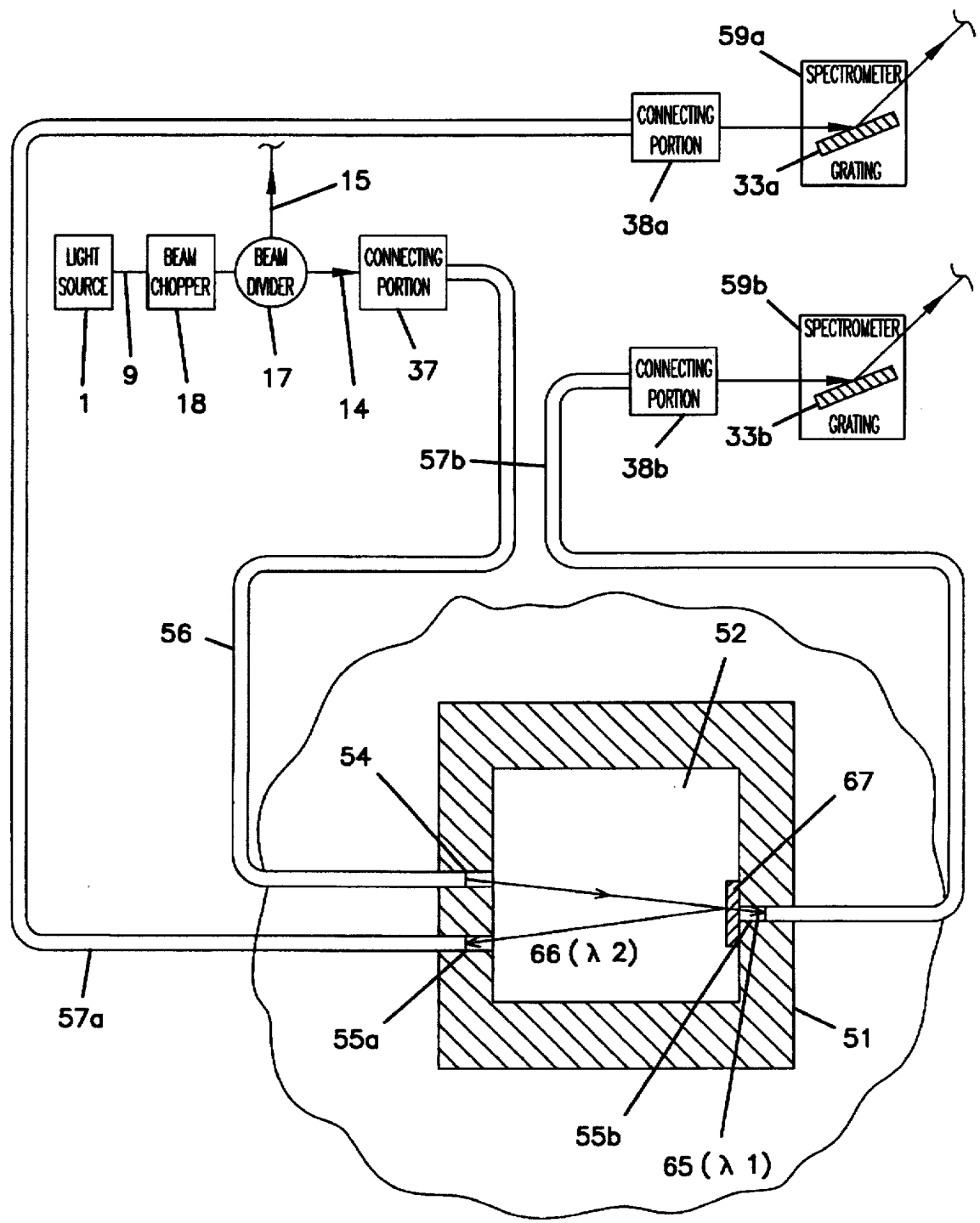
FIG. 15 is a schematic view mainly showing the head portion of an in-process film thickness monitoring system according to an eighth embodiment of the present invention.

An eighth embodiment of the present invention will be described with reference to FIG. 15. The present embodiment is different from the seventh embodiment shown in FIG. 13 in the following respects. More specifically, a reflecting mirror 53 shown in FIG. 13 is replaced with a two-way mirror 67. An optical fiber 57b for ejection is connected to the back of the two-way mirror 67 through a connecting portion 55b. Another optical fiber 57a for ejection is connected to the same side as an optical fiber 56 for injection in the same manner as FIG. 13.

The two-way mirror 67 has a wavelength selecting property. A probing beam includes the component of a characteristic waveform λ1 of an element and that of a characteristic waveform λ2 of another element. The probing beam ejected from the end of the optical fiber 56 passes through a particle flight area which is restricted by an aperture 52, and is led to the two-way mirror 67. A component 65 of the wavelength λ1 of the probing beam is transmitted through the two-way mirror 67 and then led into the optical fiber 57b. A component 66 of the wavelength λ2 is reflected by the two-way mirror 67, passes through the particle flight area which is restricted by the aperture 52, and is injected into the optical fiber 57a.

Figure 19:
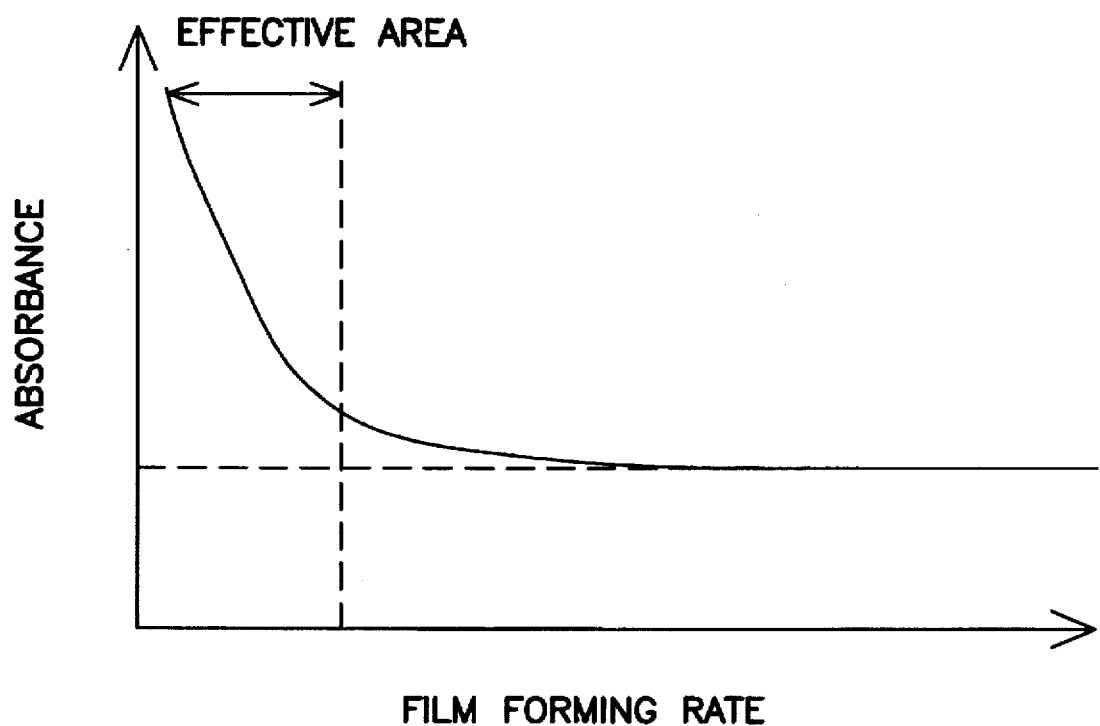
FIG. 19 is a graph showing the relationship between film forming rate and absorbance.

If a film is formed by a plurality of elements, that is, the flown particles include a plurality of elements, the film forming monitoring system according to the present embodiment can be used as a composition ratio monitor which detects an absorbance for each element, i.e., a film forming rate. As seen from FIG. 15, the optical path of the wavelength λ2 is twice as much as that of the wavelength 1. Consequently, in case the composition ratio of the element of the characteristic wavelength λ1 to that of the characteristic wavelength λ2 (i.e., a flight rate) is about 2 to 1, absorbances having the same level can be obtained for both components. Accordingly, it is easy to perform measurement with high precision in the effective area of the absorbance to the film forming rate characteristics shown in FIG. 19.

Also, if three kinds of elements or more are included in the flown particles, a beam can be separated for each characteristic wavelength on the same principle. In order to separate three kinds of wavelength components, a wavelength selective two-way mirror is provided on a connecting portion 55a of the optical fiber 57a, and a third optical fiber for ejection which receives components reflected by the two-way mirror is connected to the first two-way mirror 67 side. In case the composition ratio is greater than 2 to 1, the number of reflections is increased to make the optical path ratio greater.

Figure 16:
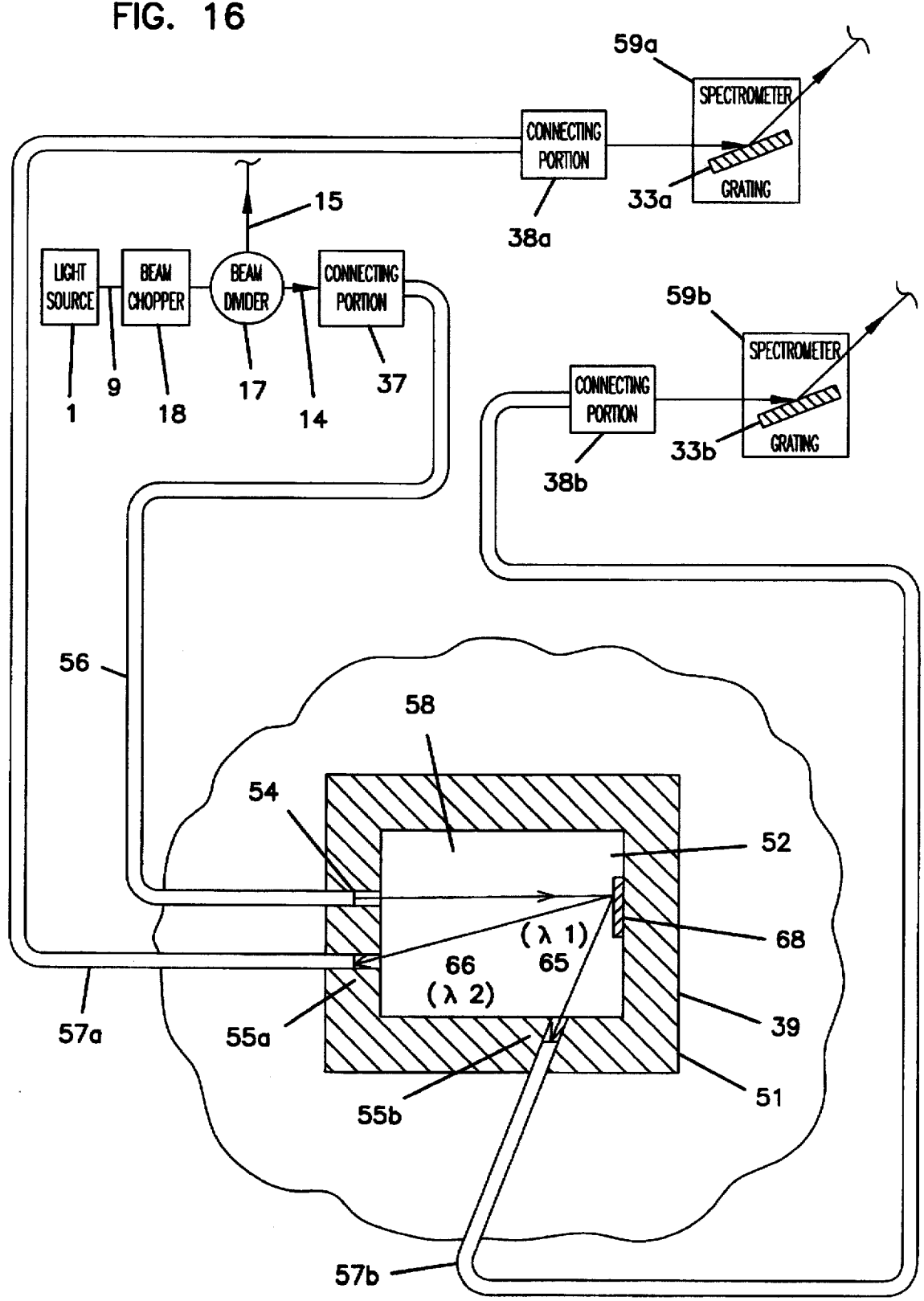
FIG. 16 is a schematic view showing a structure in which a grating is used for the head portion of the in-process film thickness monitoring system shown in FIG. 15.

As a variant of the present embodiment, a grating 68 on which an angle of reflection is varied by a wavelength may be used in place of the wavelength selective two-way mirror, and optical fiber connecting portions 55a and 55b may be provided on a place on which each wavelength component is reflected as shown in FIG. 16. Further, the number of passages through the aperture can be varied for each wavelength component by combination with the reflecting mirror.

As described in the embodiments, a variant can be applied to the present embodiment, in which the position of the head portion is controlled and moved during film formation so that the two-dimensional distribution of the film forming rate is measured.

Figure 17A:
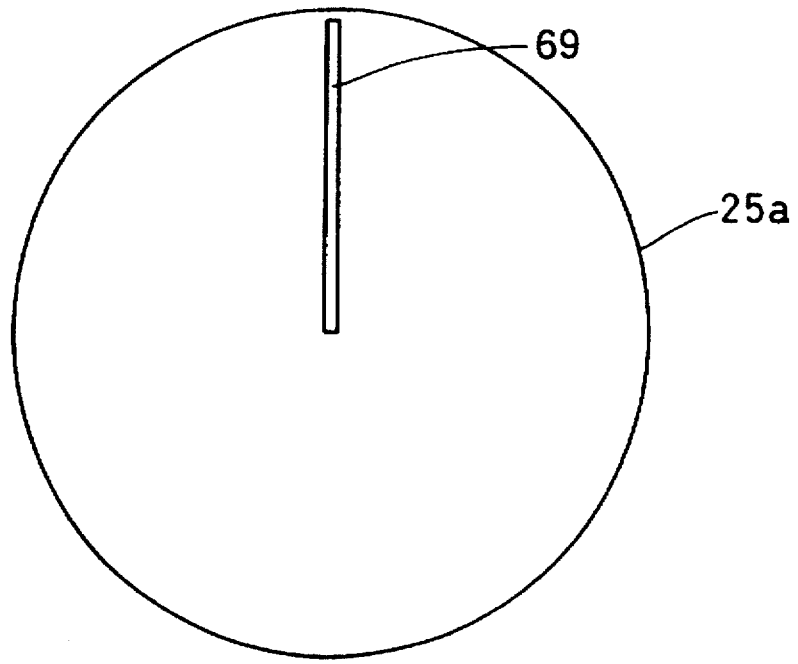
FIGS. 17A and 17B are views showing the improvement of the shielding plate provided in the in-process film thickness monitoring system according to the present invention.
Figure 17B:
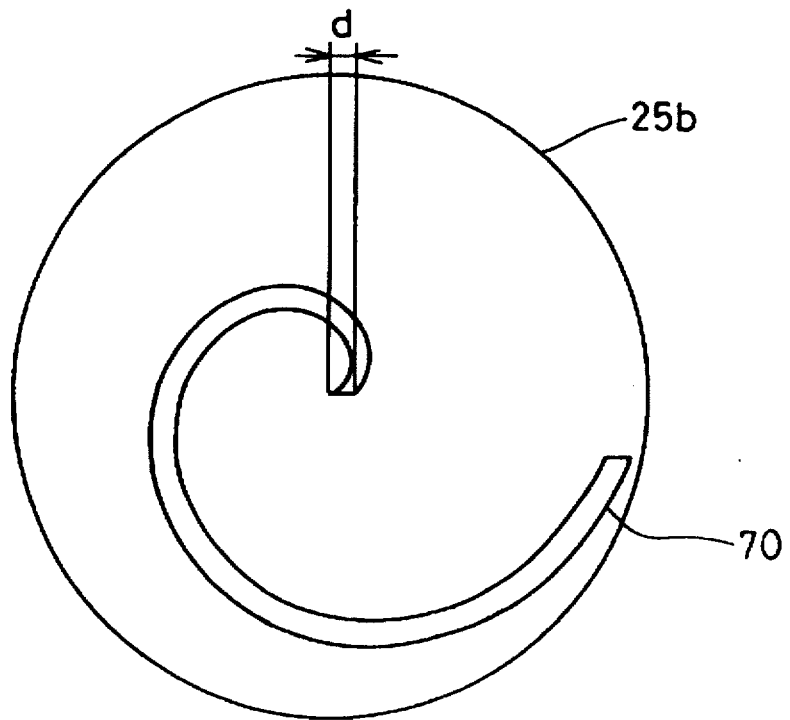
Figure 18:
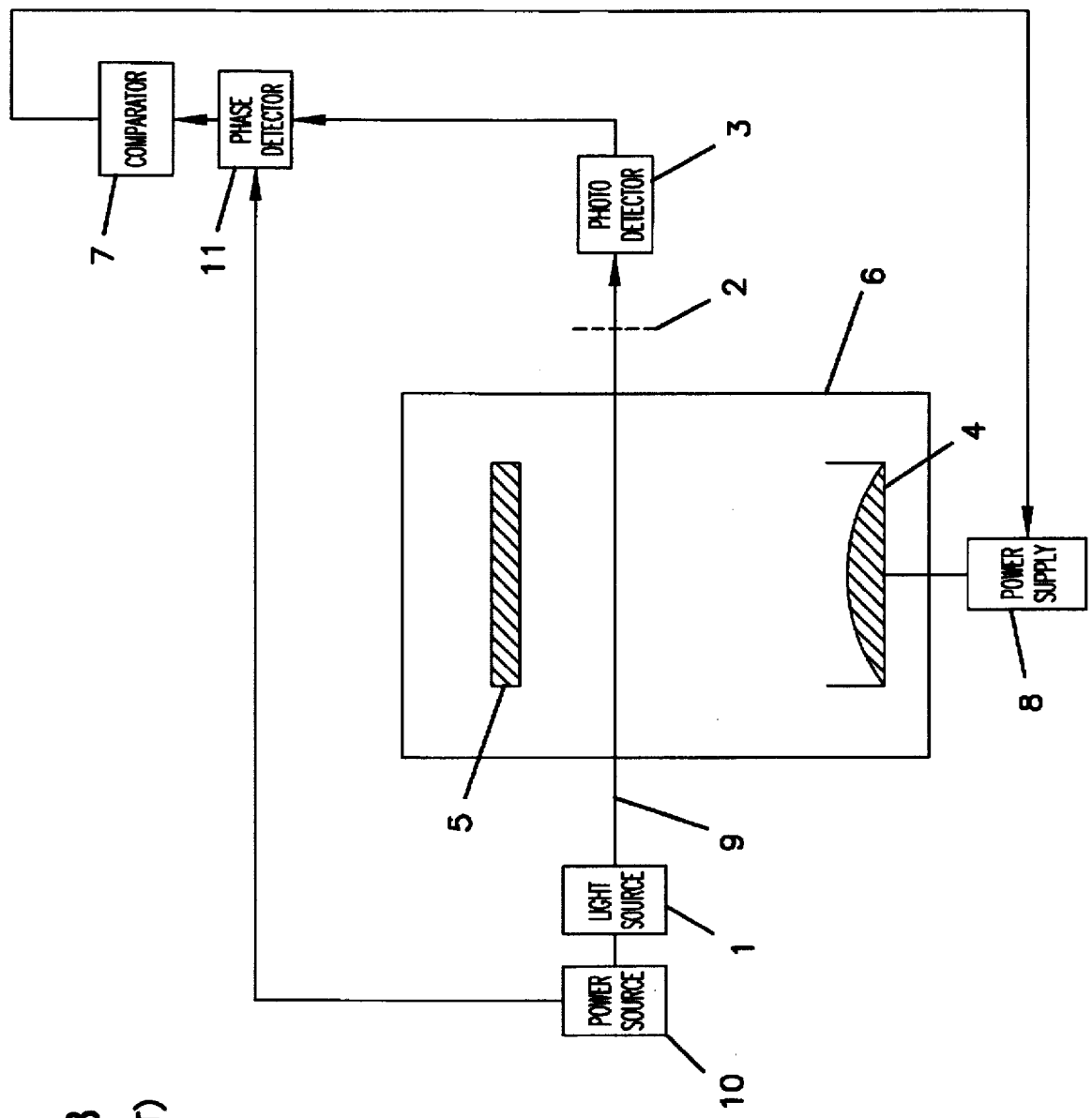
FIG. 18 is a schematic view of a film forming rate monitoring system for an evaporation apparatus according to the prior art.

A ninth embodiment of the present invention will be described with reference to FIGS. 17A and B. The present embodiment relates to the improvement of a shielding plate having an aperture for restricting the beam area of a probing beam through flown particles as shown in FIGS. 3 and 6. The shielding plate 25 according to the present embodiment has a structure in which two disk-like shielding plate members 25a and 25b shown in FIGS. 17A and B are superposed. The shielding plate member 25a has a slit-like aperture 69 formed thereon. The aperture 69 radially extends from the center of the shielding plate member 25a to the peripheral portion thereof. A shielding plate member 25b has a slit-like spiral aperture 70 formed thereon. The aperture 70 has a width of d and is held between spirals expressed by (r×θ/2π,θ) and (r×θ/2π+d,θ) in circular cylindrical coordinates.

The shielding plate member 25a is set so that the aperture 69 is oriented to correspond to a probing beam optical path. The shielding plate member 25b is superposed on the shielding plate member 25a and is rotated at a predetermined speed. An aperture for the shielding plate 25 is formed by the superposition of the aperture 69 of the shielding plate member 25a on the aperture 70 of the shielding plate member 25b. The aperture for the shielding plate 25 is radially moved with the rotation of the shielding plate member 25b. The position of the aperture can be obtained by detecting the angle of rotation of the shielding plate member 25b. Accordingly, it is possible to measure the distribution of an absorbance, i.e., a film forming rate along the radius of the shielding plate.

According to the present invention, a film forming rate, a film thickness and their two-dimensional distribution can be estimated with high precision even under conditions where it is hard to optically detect the film forming rate, as in sputtering. In case the particles of a plurality of elements are flown, the film forming rate and the film thickness can be estimated with high precision for each characteristic wavelength corresponding to each element. Consequently, a composition ratio can be estimated.

The invention may be embodied in other forms without departing from the spirit or essential characteristics thereof. The embodiments disclosed in this application are to be considered in all respects as illustrative and not restrictive, the scope of the invention is indicated by the appended claims rather than by the foregoing description, and all changes which come within the meaning and range of equivalency of the claims are intended to be embraced therein.

What is claimed is:

1. An in-process film thickness monitoring system for evaluating film formation on a substrate in a film forming system, comprising;
   a light source including the characteristic wavelength of flown particles in a film forming system;
   a beam divider for dividing a beam emitted from the light source into a probing beam which passes through the particle flight area and a reference beam which does not pass through the particle flight area;

a beam chopper for interrupting the beam before passing through the beam divider;

a spectrometer for selecting at least one characteristic wavelength component from the probing beam after passing through the particle flight area;

a probing beam detector for accepting the beam from the spectrometer and outputting a probing signal for each characteristic wavelength component;

a reference beam detector for accepting the reference beam and outputting a reference signal;

an electric filter for cutting a low-frequency component of the probing signal which is at least lower than a chopping frequency; and a data processor for estimating a film forming rate or film thickness for a plurality of characteristic wavelengths on the basis of a plurality of probing signals outputted from the probing beam detector and a reference signal outputted from the reference beam detector.

2. The in-process film thickness monitoring system according to claim 1, wherein plural sets of serial instrumentation systems including a light source, a beam divider, a spectrometer, a probe beam detector, and a data processor are provided so as to cause a plurality of probing beams to pass through different places of the particle beam area, so that the two dimensional distribution of a film forming rate or film thickness for a plurality of characteristic wavelengths is estimated.

3. The in-process film thickness monitoring system according to claim 1, wherein the film forming system includes a shielding plate provided with an aperture, and the probing beam passes behind the shielding plate, as viewed from a film-forming particle source, at a position corresponding to the aperture.

4. The in-process film thickness monitoring system according to claim 3, wherein a first disk member is superposed on a second disk member to form the shielding plate, a straight slit which extends radially is formed on the first member, and a spiral slit which extends spirally from the center to a peripheral portion is formed on the second member, and wherein the first member is set so that the straight slit is oriented to correspond to a probing beam optical path, and the second member is rotated relative to the first member so that an aperture formed by the superposition of the straight slit on the spiral slit is radially moved.

5. An in-process film thickness monitoring system for evaluating film formation on a substrate in a film forming system, comprising;

a light source including the characteristic wavelength of flown particles in a film forming system;

a beam divider for dividing a beam emitted from the light source into a probing beam which passes through the particle flight area and a reference beam which does not pass through the particle flight area;

a beam chopper for interrupting the beam before being injected into the beam divider;

an optical fiber for injection for leading the probing beam to the particle flight area;

a frame-like head portion which carries the end of the optical fiber for injection and the end of an optical fiber for ejection;

wherein the head portion is inserted in the particle flight area in the film forming system, the probing beam emitted from the end of the optical fiber for injection passes through the particle flight area which is restricted by an aperture of the head portion and is then injected into the end of the optical fiber for ejection;

wherein means for obtaining the component of the characteristic wavelength from the probing beam after passing through the particle flight area and a probing beam detector for measuring the light intensity of the component of the characteristic wavelength are connected to the other end of the optical fiber for ejection;

a reference beam detector for measuring the intensity of the reference beam; and a data processor for calculating the absorbance of the flight particles in the film forming system on the basis of a probing signal outputted from the probing beam detector and a reference signal outputted from the reference beam detector, and estimating a film forming rate from the absorbance.

6. The in-process film thickness monitoring system according to claim 5, wherein the head portion includes one or more reflecting mirror and the probing beam emitted from the end of the optical fiber for injection passes through the particle flight area plural times by being reflected by the reflecting mirror, the particle flight area being restricted by the aperture of the head portion and is then injected into the end of the optical fiber for ejection.

7. The in-process film thickness monitoring system according to claim 5, wherein the light source has a plurality of characteristic wavelengths, and the head portion has a structure in which at least one reflecting mirror is a two-way mirror, a part of the wavelength components of the probing beams which are emitted from the end of the optical fiber for injection and pass through the particle flight area pass through the two-way mirror and are sent to an end of a first optical fiber for ejection, and other wavelength components are reflected by the two-way mirror, pass through the particle flight area and are sent to another optical fiber for ejection, and wherein means for obtaining the component of the characteristic wavelength from the probing beam after passing through the particle flight area and a probing beam detector for measuring the light intensity of the component of the characteristic wavelength are connected to the other end of the first optical fiber for ejection.

8. The in-process film thickness monitoring system according to claim 7, wherein a spectrometer having a grating with a rotary shaft is used for obtaining the component of the characteristic wavelength at a second end of the optical fibers for ejection, and wherein each optical fiber for ejection is connected to the spectrometer so that beams emitted from the optical fibers for ejection are directed perpendicularly with respect to the rotary shaft of the grating of the spectrometer and in parallel with each other and spaced so that they do not interfere with each other.

9. An in-process film thickness monitoring system for evaluating film formation on a substrate in a film forming system, comprising:

a light source including the characteristic wavelength of flown particles to be deposited on a substrate in a film forming system;

a beam divider for dividing a beam emitted from the light source into a probing beam that passes through a particle flight area and a reference beam that does not pass through the particle flight area;

photodetectors for measuring the light intensities of the probing beam that passed through the particle flight area and the reference beam;

optical filters for passing only the characteristic wavelength component of the beam to the photodetectors; and a data processor for calculating the absorbance of the flown particles in the film forming system on the basis of a reference signal and a probing signal outputted from the photodetectors and estimating a film forming rate from the absorbance, wherein the film forming system includes a shielding plate provided with an aperture, and the probing beam passes behind the shielding plate, as viewed from a film-forming particle source, at a position corresponding to the aperture.

10. The in-process film thickness monitoring system according to claim 9, wherein a first disk member is superposed on a second disk member to form the shielding plate, a straight slit which extends radially is formed on the first member, and a spiral slit which extends spirally from the center to a peripheral portion is formed on the second member, and wherein the first member is set so that the straight slit is oriented to correspond to a probing beam optical path, and the second member is rotated relative to the first member so that an aperture formed by superposition of the straight slit on the spiral slit is radially moved.

11. An in-process film thickness monitoring system for evaluating film formation on a substrate in a film forming system, comprising:

a light source including the characteristic wavelength of flown particles to be deposited on a substrate in a film forming system;

a beam divider for dividing a beam emitted from the light source into a probing beam that passes through a particle flight area and a reference beam that does not pass through the particle flight area;

photodetectors for measuring the light intensities of the probing beam that passed through the particle flight area and the reference beam;

optical filters for passing only the characteristic wavelength component of the beam to the photodetectors; and a data processor for calculating the absorbance of the flown particles in the film forming system on the basis of a reference signal and a probing signal outputted from the photodetectors and estimating a film forming rate from the absorbance, wherein the probing beam passes behind the substrate as viewed from a film-forming particle source in the film forming system.

12. An in-process film thickness monitoring system for evaluating film formation on a substrate in a film forming system, comprising:

a light source including the characteristic wavelength of flown particles to be deposited on a substrate in a film forming system;

a beam divider for dividing a beam emitted from the light source into a probing beam that passes through a particle flight area and a reference beam that does not pass through the particle flight area;

photodetectors for measuring the light intensities of the probing beam that passed through the particle flight area and the reference beam;

optical filters for passing only the characteristic wavelength component of the beam to the photodetectors; and a data processor for calculating the absorbance of the flown particles in the film forming system on the basis of a reference signal and a probing signal outputted from the photodetectors and estimating a film forming rate from the absorbance, wherein the light source and the beam divider cause a plurality of probing beams to pass through different places in the particle flight area, the photodetector measures the intensity of the probing beams that passed through the particle flight area, and the data processor estimates the two-dimensional distribution of the film forming rate or film thickness on the basis of a plurality of probing signals and reference signals outputted from the photodetectors.

13. An in-process film thickness monitoring system for evaluating film formation on a substrate in a film forming system, comprising:

a light source having a plurality of wavelengths, including the characteristic wavelength of flown particles to be deposited on a substrate in a film forming system;

a beam divider for dividing a beam emitted from the light source into a probing beam that passes through a particle flight area and a reference beam that does not pass through the particle flight area;

a beam chopper for interrupting the beam from the light source before the beam reaches the beam divider;

a first optical fiber that carries the probing beam for injection to the particle flight area;

a second optical fiber that carries the probing beam for ejection from the particle flight area; and a frame-like head portion, disposed in the particle flight area in the film forming system, that carries a first end of the first optical fiber from which the probing beam is injected into the particle flight area and a first end of the second optical fiber into which the probing beam is injected after passing through the particle flight area, the head portion having an aperture that restricts the particle flight area through which the probing beam passes, the head portion being provided with a grating through which the direction of reflection is varied depending on wavelength, whereby a part of the wavelength components of the probing beam is directed by the grating to the second optical fiber for ejection, and other wavelength components are directed to a third optical fiber for ejection;

wherein means for obtaining the component of the characteristic wavelength from the probing beam after passing through the particle flight area and a probing beam detector for measuring the light intensity of the component of the characteristic wavelength are connected to a second end of the second optical fiber.

14. A method for monitoring a film thickness formed on a substrate by flown particles, comprising the steps of:

chopping beams emitted from a light source, including the characteristic wavelength of the flown particles to be deposited on a substrate in a film forming system, in a predetermined cycle;

dividing the beams into a probing beam that passes through a particle flight area and a reference beam that does not pass through the particle flight area;

obtaining a probing signal from the component of the characteristic wavelength of the probing beam after passing through the particle flight area;

obtaining a reference signal from the component of the characteristic wavelength of the reference beam;

comparing the phases of both signals so as to cut noise components; and calculating an absorbance for flown particles in the film forming system from the level ratios of the signals so as to estimate a film forming rate from the absorbance, wherein a plurality of probing beams pass through different places of the particle flight area, and two-dimensional distribution of a film forming rate is estimated from a plurality of probing signals and a reference signal.

15. A method for monitoring a film thickness formed on a substrate by flown particles, comprising the steps of:

chopping beams emitted from a light source, including the characteristic wavelength of the flown particles to be deposited on a substrate in a film forming system, in a predetermined cycle;

dividing the beams into a probing beam that passes through a particle flight area and a reference beam that does not pass through the particle flight area;

obtaining a probing signal from the component of the characteristic wavelength of the probing beam after passing through the particle flight area;

obtaining a reference signal from the component of the characteristic wavelength of the reference beam;

comparing the phases of both signals so as to cut noise components; and calculating an absorbance for flown particles in the film forming system from the level ratios of the signals so as to estimate a film forming rate from the absorbance, wherein the probing beam is led to the film forming system by means of a first optical fiber, the probing beam emitted from an end of the first optical fiber is caused to pass through the particle forming area and then is injected into a second optical fiber, and the probing beam is led out of the film forming system by the second optical fiber, and the probing beam emitted from the first optical fiber is caused to pass through the particle flight area plural times by means of a reflecting mirror and then injected into the second optical fiber.

16. A method for monitoring a film thickness formed on a substrate by flown particles, comprising the steps of:

chopping beams emitted from a light source, including the characteristic wavelength of the flown particles to be deposited on a substrate in a film forming system, in a predetermined cycle;

dividing the beams into a probing beam that passes through a particle flight area and a reference beam that does not pass through the particle flight area;

obtaining a probing signal from the component of the characteristic wavelength of the probing beam after passing through the particle flight area;

obtaining a reference signal from the component of the characteristic wavelength of the reference beam;

comparing the phases of both signals so as to cut noise components; and calculating an absorbance for flown particles in the film forming system from the level ratios of the signals so as to estimate a film forming rate from the absorbance, wherein the probing beam is led to the film forming system by means of a first optical fiber, the probing beam emitted from an end of the first optical fiber is caused to pass through the particle forming area and then is injected into a second optical fiber, and the probing beam is led out of the film forming system by the second optical fiber, and a part of the wavelength components of the probing beam that is emitted from the end of the first optical fiber and passes through the particle flight area is caused to pass through a two-way mirror having wavelength selectivity and injected into the second optical fiber, and other wavelength components are reflected by the two-way mirror, are caused to pass through the particle flight area and are injected into a third optical fiber for leading the other wavelength component out of the film forming system.

17. A method for monitoring a film thickness formed on a substrate by flown particles, comprising the steps of:

chopping beams emitted from a light source, including the characteristic wavelength of the flown particles to be deposited on a substrate in a film forming system, in a predetermined cycle;

dividing the beams into a probing beam that passes through a particle flight area and a reference beam that does not pass through the particle flight area;

obtaining a probing signal from the component of the characteristic wavelength of the probing beam after passing through the particle flight area;

obtaining a reference signal from the component of the characteristic wavelength of the reference beam;

comparing the phases of both signals so as to cut noise components; and calculating an absorbance for flown particles in the film forming system from the level ratios of the signals so as to estimate a film forming rate from the absorbance, wherein the probing beam is led to the film forming system by means of a first optical fiber, the probing beam emitted from an end of the first optical fiber is caused to pass to the particle forming area and then is injected into a second optical fiber, and the probing beam is led out of the film forming system by the second optical fiber, and a part of the wavelength components of the probing beam that is emitted from the end of the first optical fiber and passes through the particle flight area is caused to pass to a grating through which the direction reflection is varied depending on wavelength so that different wavelengths of the probing beam are caused to pass through particle flight area over different distances and directed to one of a plurality of the second optical fibers to be led out of the film forming system.

18. A method for monitoring a film thickness formed on a substrate by flown particles, comprising the steps of:

chopping beams emitted from a light source, including the characteristic wavelength of the flown particles to be deposited on a substrate in a film forming system, in a predetermined cycle;

dividing the beams into a probing beam that passes through a particle flight area and a reference beam that does not pass through the particle flight area;

obtaining a probing signal from the component of the characteristic wavelength of the probing beam after passing through the particle flight area;

obtaining a reference signal from the component of the characteristic wavelength of the reference beam;

comparing the phases of both signals so as to cut noise components; and calculating an absorbance for flown particles in the film forming system from the level ratios of the signals so as to estimate a film forming rate from the absorbance, wherein the probing beam is led to the film forming system by means of a first optical fiber, the probing beam emitted from an end of the first optical fiber is caused to pass through the particle forming area and then is injected into a second optical fiber, and the probing beam is led out of the film forming system by the second optical fiber, and the first and second optical fibers have ends carried by a head portion that is inserted in the particle flying area in order to pass the probing beam emitted from the end of the first optical fiber through the particle flying area and into the end of the second optical fiber, the head portion being moved in the particle flight area so that the two-dimensional distribution of a film forming rate is estimated.

* * * * *